United States Patent
Sesha

(10) Patent No.: US 9,642,801 B2
(45) Date of Patent: May 9, 2017

(54) AND POTENT TAPENTADOL DOSAGE FORMS

(75) Inventor: Ramesh Sesha, Windsor, NJ (US)

(73) Assignee: Gruenenthal GmbH, Aachen (DE)

( * ) Notice: Subject to any disclaimer, the term of this patent is extended or adjusted under 35 U.S.C. 154(b) by 184 days.

(21) Appl. No.: 13/091,871

(22) Filed: Apr. 21, 2011

(65) Prior Publication Data

US 2011/0281855 A1 Nov. 17, 2011

Related U.S. Application Data

(63) Continuation of application No. PCT/US2009/005866, filed on Oct. 29, 2009.

(60) Provisional application No. 61/197,625, filed on Oct. 30, 2008, provisional application No. 61/205,312, filed on Jan. 21, 2009, provisional application No. 61/268,630, filed on Jun. 15, 2009.

(51) Int. Cl.
| | | |
|---|---|---|
| A61K 31/137 | (2006.01) |
| A61K 31/485 | (2006.01) |
| A61K 9/107 | (2006.01) |
| A61K 9/16 | (2006.01) |
| A61K 9/20 | (2006.01) |
| A61K 9/24 | (2006.01) |
| A61K 9/28 | (2006.01) |
| A61K 9/50 | (2006.01) |
| A61K 31/135 | (2006.01) |
| A61K 31/35 | (2006.01) |
| A61K 45/06 | (2006.01) |

(52) U.S. Cl.
CPC .......... *A61K 9/1075* (2013.01); *A61K 9/1611* (2013.01); *A61K 9/1617* (2013.01); *A61K 9/1635* (2013.01); *A61K 9/1652* (2013.01); *A61K 9/209* (2013.01); *A61K 9/2077* (2013.01); *A61K 9/284* (2013.01); *A61K 9/2866* (2013.01); *A61K 9/5078* (2013.01); *A61K 9/5084* (2013.01); *A61K 31/135* (2013.01); *A61K 31/137* (2013.01); *A61K 31/35* (2013.01); *A61K 31/485* (2013.01); *A61K 45/06* (2013.01)

(58) Field of Classification Search
USPC ...................................... 514/225.5
See application file for complete search history.

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,034,758 A | 7/1977 | Theeuwes et al. |
| 4,077,407 A | 3/1978 | Theeuwes et al. |
| 4,783,337 A | 11/1988 | Wong et al. |
| 5,071,607 A | 12/1991 | Ayer et al. |
| 5,472,943 A | 12/1995 | Crain et al. |
| 5,866,164 A | 2/1999 | Kuczynski et al. |
| 6,103,258 A | 8/2000 | Simon |
| 6,228,863 B1 | 5/2001 | Palermo et al. |
| 6,248,737 B1 | 6/2001 | Buschmann et al. |
| 6,277,384 B1 | 8/2001 | Kaiko et al. |
| 6,309,668 B1 | 10/2001 | Bastin et al. |
| 6,375,957 B1 | 4/2002 | Kaiko et al. |
| 6,475,494 B2 | 11/2002 | Kaiko et al. |
| 6,559,159 B2 | 5/2003 | Carroll et al. |
| 6,696,066 B2 | 2/2004 | Kaiko et al. |
| 6,696,088 B2 | 2/2004 | Oshlack et al. |
| 6,716,449 B2 | 4/2004 | Oshlack |
| 6,765,010 B2 | 7/2004 | Crain et al. |
| RE39,593 E | 4/2007 | Buschmann et al. |
| 7,332,142 B2 | 2/2008 | Telford et al. |
| 7,658,939 B2 | 2/2010 | Oshlack et al. |
| 7,682,632 B2 | 3/2010 | Oshlack et al. |
| 7,718,192 B2 | 5/2010 | Oshlack et al. |
| 7,842,309 B2 | 11/2010 | Oshlack et al. |
| 7,842,311 B2 | 11/2010 | Oshlack et al. |
| 8,236,351 B2 | 8/2012 | Oshlack et al. |
| 8,357,399 B2 | 1/2013 | Oshlack et al. |
| 8,586,088 B2 | 11/2013 | Oshlack et al. |

(Continued)

FOREIGN PATENT DOCUMENTS

| | | |
|---|---|---|
| AU | 2009 340504 A1 | 8/2010 |
| CA | 2 741 984 A1 | 8/2010 |

(Continued)

OTHER PUBLICATIONS

Stegmann et al. Curr Med Res Opin. Oct. 10, 2008 (Epup), vol. 24. No. 11, pp. 3185-3196.*
NDA 22-304 "Clinical Pharmacology and Biopharmaceutics Review", Center for Drug Evaluation and Research, Jan. 23, 2008, 131 pages.*
Tzschentke, et al; "(−)-(1R,2R)-3-(3-Dimethylamino-1-ethyl-2-methyl-propyl)-phenol hydrochloride (Tapentadol HCL): a novel μ-opioid receptor agonist/norepinephrine reuptake inhibitor with broad-spectrum analgesic properties"; The Journal of Pharmacology and Experimental Therapeutics, 2007, vol. 323, No. 1, pp. 265-276.
Raffa, et al., "Mechanistic and functional differentiation of tapentadol and tramadol"; Expert Opinion on Pharmacotherapy, 2012, 13(10), pp. 1437-1449.

(Continued)

*Primary Examiner* — Savitha Rao
*Assistant Examiner* — Gregg Polansky
(74) *Attorney, Agent, or Firm* — Norris McLaughlin & Marcus, P.A.

(57) ABSTRACT

The present invention provides a dosage form comprising at least one form of tapentadol, with or without a second analgesic, and at least one opioid antagonist, wherein tapentadol is present in an optimal or suboptimal amount and the said antagonist is present in an amount effective to improve the efficacy and or reduce the side effects of tapentadol. The present invention further provides a method of treating pain and pain related conditions by administering to a patient in need thereof, a dosage form comprising at least one form of tapentadol, with or without a second analgesic, and at least one opioid antagonist, wherein tapentadol is present in an optimal or suboptimal amount and the said antagonist is present in an amount effective to improve the efficacy and or reduce the side effects of tapentadol.

22 Claims, 17 Drawing Sheets

(56) References Cited

U.S. PATENT DOCUMENTS

| | | |
|---|---|---|
| 8,846,090 B2 | 9/2014 | Brögmann et al. |
| 8,846,091 B2 | 9/2014 | Brögmann et al. |
| 8,936,812 B2 | 1/2015 | Oshlack et al. |
| 8,946,290 B2 | 2/2015 | Christoph |
| 9,278,073 B2 | 3/2016 | Oshlack et al. |
| 2003/0073714 A1* | 4/2003 | Breder et al. ............ 514/282 |
| 2003/0143269 A1 | 7/2003 | Oshlack et al. |
| 2004/0024004 A1* | 2/2004 | Sherman et al. ......... 514/282 |
| 2004/0092542 A1 | 5/2004 | Oshlack et al. |
| 2004/0176402 A1 | 9/2004 | Oshlack et al. |
| 2004/0186121 A1 | 9/2004 | Oshlack et al. |
| 2004/0242617 A1 | 12/2004 | Christoph |
| 2005/0058706 A1 | 3/2005 | Bartholomaeus et al. |
| 2005/0095291 A1 | 5/2005 | Oshlack et al. |
| 2005/0181046 A1 | 8/2005 | Oshlack et al. |
| 2005/0191244 A1 | 9/2005 | Bartholomaus et al. |
| 2005/0245483 A1 | 11/2005 | Brögmann et al. |
| 2005/0245556 A1 | 11/2005 | Brögmann et al. |
| 2005/0276837 A1 | 12/2005 | Anderson et al. |
| 2006/0039970 A1 | 2/2006 | Oshlack et al. |
| 2008/0305167 A2 | 12/2008 | Oshlack et al. |
| 2008/0306104 A2 | 12/2008 | Oshlack et al. |
| 2008/0311198 A2 | 12/2008 | Oshlack et al. |
| 2008/0311199 A2 | 12/2008 | Oshlack et al. |
| 2009/0005458 A1* | 1/2009 | Rombout et al. ......... 514/654 |
| 2009/0012180 A1 | 1/2009 | Lange et al. |
| 2010/0331425 A1 | 12/2010 | Rombout et al. |
| 2011/0097404 A1 | 4/2011 | Oshlack et al. |
| 2012/0016023 A1 | 1/2012 | Christoph |
| 2012/0034304 A1 | 2/2012 | Bartholomaeus et al. |
| 2012/0041071 A1 | 2/2012 | Rombout et al. |
| 2012/0108621 A1 | 5/2012 | Brögmann et al. |
| 2012/0183612 A1 | 7/2012 | Brögmann et al. |
| 2012/0288565 A1 | 11/2012 | Oshlack et al. |
| 2013/0237608 A1 | 9/2013 | Bartholomaeus et al. |
| 2013/0251789 A1 | 9/2013 | Oshlack et al. |
| 2014/0045877 A1 | 2/2014 | Brögmann et al. |
| 2014/0045878 A1 | 2/2014 | Brögmann et al. |
| 2014/0099369 A1 | 4/2014 | Oshlack et al. |
| 2014/0296277 A1 | 10/2014 | Brögmann et al. |
| 2015/0005335 A1 | 1/2015 | Brögmann et al. |
| 2015/0182467 A1 | 7/2015 | Oshlack et al. |
| 2015/0231086 A1 | 8/2015 | Oshlack et al. |

FOREIGN PATENT DOCUMENTS

| | | |
|---|---|---|
| CN | 10 2281876 A | 12/2011 |
| EP | 1 985 292 A1 | 10/1986 |
| EP | 693 475 | 1/1996 |
| EP | 2 352 494 A1 | 8/2011 |
| JP | 2003 522144 A | 7/2003 |
| JP | 2005-506367 A | 3/2005 |
| JP | 2005 507387 A | 3/2005 |
| JP | 2005 528375 A | 9/2005 |
| KR | 2011 0081880 A | 7/2011 |
| MX | 2011 004455 A | 5/2011 |
| RU | 2 305 562 C2 | 9/2005 |
| RU | 2 305 562 C2 | 9/2007 |
| RU | 2 325 905 C2 | 6/2008 |
| WO | 00/01377 A2 | 1/2000 |
| WO | 01/58447 A1 | 8/2001 |
| WO | 03 035053 A1 | 5/2003 |
| WO | 2007 087452 A2 | 8/2007 |
| WO | 2008027442 A2 | 3/2008 |
| WO | 2008 128739 A1 | 10/2008 |
| WO | 2010 096045 | 8/2010 |

OTHER PUBLICATIONS

Leri, "Co-administration of opioid agonists and antagonists in addiction and pain medicine"; Expert Opinion Pharmacother. (2008) 9(8): 1387-1396.

Hochberg's (Biometrik 75: 800 (1988).

Encyclopedia of Polymer Science and Technology, vol. 10, 1969, John Wiley & Sons, Inc., Table of Contents and pp. 228-306.

Enciklopedija lekarstv, Moscow, RLS 2001—Drug Encyclopedia, 8th Edition, Editor-in-Chief Yu F. Krylov; p. 879; English language translation provided.

* cited by examiner

FIGURE 4

| Patient Group | Group 1 (Placebo+Placebo) Co-Administration | Group 2 Tap 50 mg+ Placebo Co-Administration | Group 3 Tap 50 mg + N1 (0.1 mg) Co-Administration | Group 4 Tap 50 mg + N2 (0.1 mg) Co-Administration | Group 5 Tap 50 mg + N3 (1 mg) Co-Administration |
|---|---|---|---|---|---|
| Drug Dosage Dosage Type | | | | | |
| No. of Patients | 51 | 50 | 51 | 52 | 50 |
| Nausea | 18.00% | 35.00% | 21.00% | 30.00% | 40.00% |
| Vomitting | 4.00% | 16.00% | 12.00% | 14.00% | 15.00% |
| Dizziness | 19.00% | 27.00% | 14.00% | 16.00% | 20.00% |
| Head Ache | 51.00% | 55.00% | 48.00% | 51.00% | 53.00% |

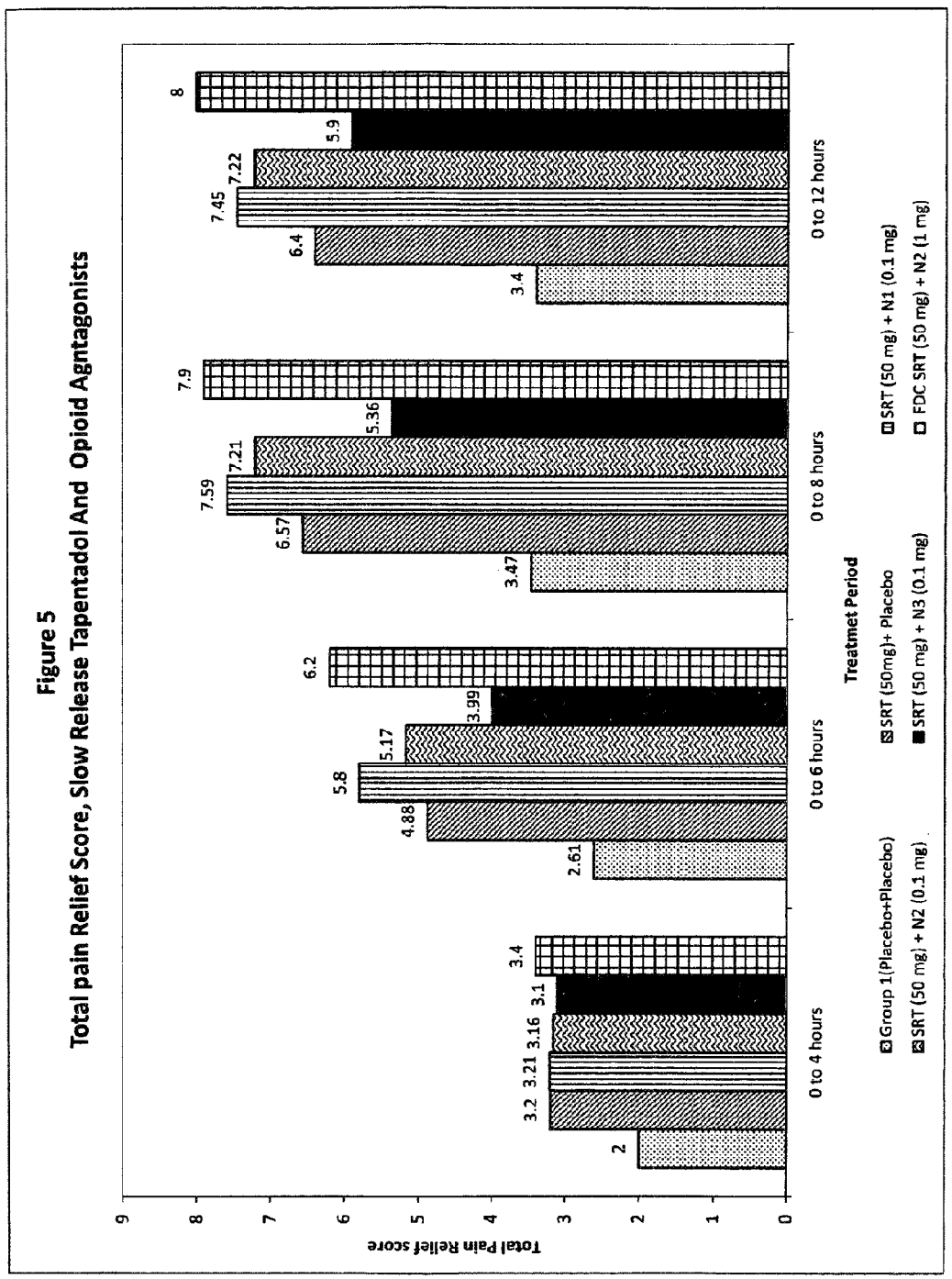

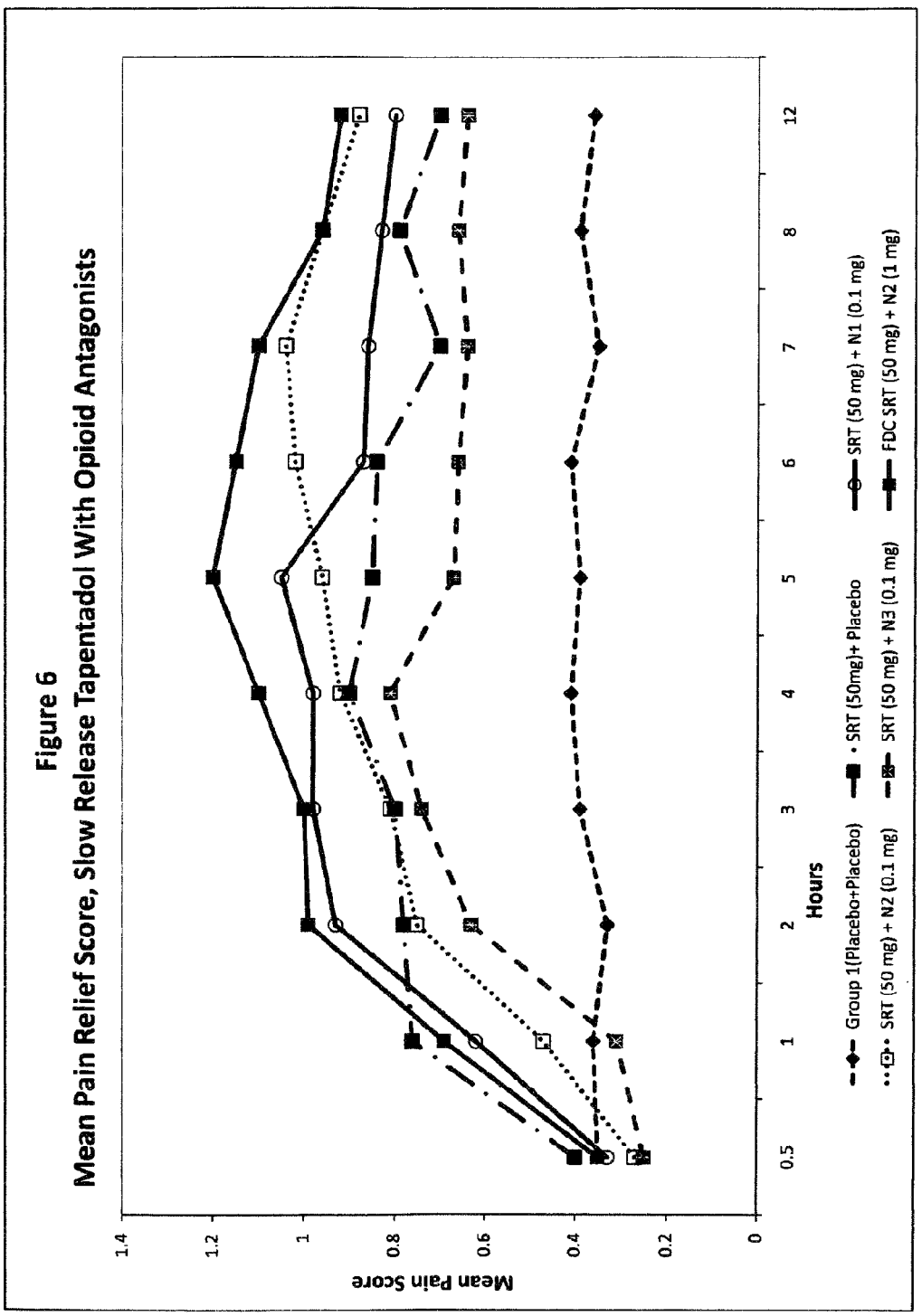

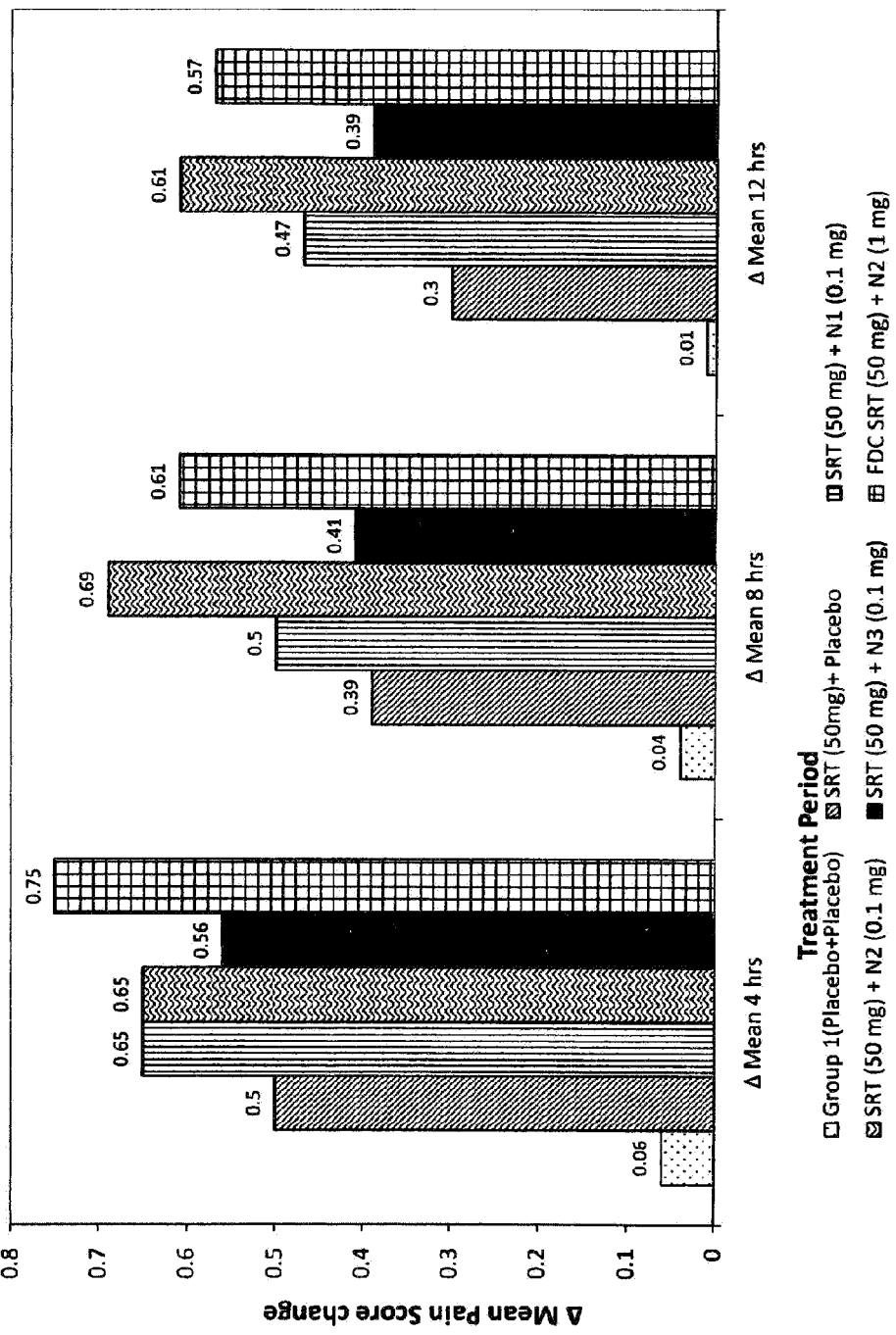

FIGURE 8

| Patient Group | Group 1 | Group 2 | Group 3 | Group 4 | Group 5 | Group 6 |
|---|---|---|---|---|---|---|
| Example | Placebo | Example 2 | Example 2 | Example 2 | Example 2 | Example 1 FDC |
| Drug Dosage | Placebo+Placebo | SRT 50 mg + Placebo | SRT 50 mg+ N1 (0.1 mg) | SRT 50 mg+ N2( 0.1 mg) | SRT 50 mg+ N3 (0.1 mg) | SRT 50 mg+ N2(1 mg) |
| Dosage Type | Co-Administration | Co-Administration | Co-Administration | Co-Administration | Co-Administration | Fixed Dose |
| No. of Patients | 51 | 49 | 53 | 50 | 52 | 52 |
| Nausea | 18.00% | 31.00% | 21.00% | 28.00% | 38.00% | 28.00% |
| Vomitting | 4.00% | 13.00% | 10.00% | 12.00% | 15.00% | 9.00% |
| Dizziness | 19.00% | 22.00% | 11.00% | 17.00% | 19.00% | 18.00% |
| Head Ache | 51.00% | 48.00% | 41.00% | 43.00% | 49.00% | 43.00% |

Total Pain Relief Tapentadol+ Naproxen with Naltrexone

FIGURE 17

| Patient Group | Group 1 | Group 2 | Group 3 | Group 4 | Group 5 |
|---|---|---|---|---|---|
| Drugs | (Placebo+Placebo) | Tapentadol 50 mg + Placebo | Tapentadol 50 mg + MethylNaltrexone(0.01 mg) | Tapentadol 50 mg + MethylNaltrexone (0.1 mg) | Tapentadol 50 mg + MethylNaltrexone(1 mg) |
| Dosage Type | Co-Administration | Co-Administration | Co-Administration | Co-Administration | Co-Administration |
| No. of Patients | 51 | 50 | 51 | 52 | 50 |
| Constipation | 18.00% | 35.00% | 45.00% | 21.00% | 43.00% |

AND POTENT TAPENTADOL DOSAGE FORMS

RELATED APPLICATIONS

This application is a continuation of International Patent Application No. PCT/US2009/005866, filed on Oct. 29, 2009, which, in turn, claims priority from U.S. Provisional Patent Applications Ser. No. 61/197,625 filed on Oct. 30, 2008, Provisional Patent Application Ser. No. 61/205,312 filed on Jan. 21, 2009, and Provisional Patent Application Ser. No. 61/268,630 filed on Jun. 15, 2009, all of which are incorporated herein by reference.

FIELD OF THE INVENTION

The present invention is related to a pharmaceutical dosage form comprising at least one form of tapentadol, with or without a second analgesic, and at least one opioid antagonist wherein the said antagonist improves the efficacy and to reduce the side effects of tapentadol. The dosage forms include immediate release and slow release dosage forms of at least one form of tapentadol and least one opioid antagonist wherein the said tapentadol is in an optimal or suboptimal amount.

BACKGROUND OF THE INVENTION

Tapentadol, 3-(3-Dimethylamino-1-ethyl-2-methyl-propyl)-phenol) is a centrally acting analgesic with a dual mode of action: mu-opioid receptor agonism and noradrenaline reuptake inhibition. Its dual mode of action provides analgesia at similar levels of more potent narcotic analgesics such as hydrocodone, oxycodone, and morphine with a more tolerable side effect profile. Tapentadol was first disclosed and claimed in European patent no. EP 693,475, US. Pat. No. 6,248,737 and US. Pat. RE39,593. The immediate release pharmaceutical composition of tapentadol is the subject of the United States Food and Drug Administration Approved New Drug Application number 22-304.

There are a number of classes of analgesic compounds used for treating acute and chronic pain. These include acetaminophen, NSAIDs such as naproxen, meloxicam etc, CINODS such as naproxcinod, OPIATES such as morphine, tramadol, tapentadol, oxycodone etc, GABA analogues such as pregabalin and SNRIs such as duloxetine etc.

Pregabalin, a GABA analogue, is an anticonvulsant drug used for neuropathic pain, as an adjunct therapy for partial seizures, and in generalized anxiety disorder. Pregabalin was designed as a more potent successor to gabapentin and it is marketed by Pfizer under the trade name Lyrica®. In general, pregabalin reduces the release of several neurotransmitters, including glutamate, noradrenaline, and substance P. Gabapentin is another GABA analogue similar to Pregabalin and was initially synthesized to mimic the chemical structure of the neurotransmitter gamma-aminobutyric acid (GABA), but is not believed to act on the same brain receptors. Its exact mechanism of action is unknown, but its therapeutic action on neuropathic pain is thought to involve voltage-gated N-type calcium ion channels. It is thought to bind to the $\alpha2\delta$ subunit of the voltage-dependent calcium channel in the central nervous system.

NSAIDs non-steroidal anti-inflammatory drug (NSAIDs) include but are not limited to Diclofenac; Celecoxib; Diflunisal; Etodolac; Fenoprofen; Ibuprofen; Indomethacin; Ketoprofen, and, Ketorolac and used for treating pain.

Serotonin Norepinephrine Reuptake inhibitors (SNRIs) are a class of antidepressant used in the treatment of clinical depression, anxiety disorders, obsessive-compulsive disorder, attention deficit hyperactivity disorder (ADHD) and chronic neuropathic pain. They act upon two neurotransmitters in the brain that are known to play an important part in mood, namely, serotonin and norepinephrine. Examples of SNRIs include Venlafaxine, duloxetine, milnacipran and desvenlafaxine etc.

The drugs acting on 5-HT receptors are usually designated as 5-HTagonists. The 5 HT1 agonists are known and used for the treatment of headaches including migraine headache. They were first introduced in the 1990s. While effective at treating individual headaches, they are neither a preventative nor a cure. Triptans include sumatriptan, (Imitrex, Imigran), rizatriptan (Maxalt), naratriptan (Amerge, Naramig), zolmitriptan (Zomig), eletriptan (Relpax), almotriptan (Axert, Almogran), and frovatriptan (Frova, Migard).

Cyclo-oxygenase-(COX)-inhibiting nitric oxide donator or "CINODs" have a nitric oxide (NO)-releasing group and are also designated No-NSAIDs. These include but not limited to naproxcinod among others.

Proton Pump Inhibitors ("PPI"s) are a group of drugs that produce pronounced and long-lasting reduction of gastric acid production. PPIs structurally are usually benzimidazole and benzimidazole—like derivatives. The key PPIs include Clinically used proton pump inhibitors: Omeprazole (brand names: Losec, Prilosec, Zegerid, ocid), Lansoprazole (brand names: Prevacid, Zoton, Inhibitol), Esomeprazole (brand names: Nexium), Pantoprazole (FORMULA 15) (brand names: Protonix, Somac, Pantoloc, Pantozol, Zurcal, Pan), Rabeprazole (brand names: Rabecid, Aciphex, Pariet, Rabeloc. Dorafem:

Despite the benefits derived from these pain drugs, one area of concern relates to the incidence of unwanted side effects caused by these drugs. Thus there is an unmet need to develop pharmaceutical dosage forms comprising tapentadol such that the dosage forms with enhanced analgesic properties with as minimal side effects as possible. Hence it is desirable to develop dosage forms with reduced dosages of these drugs to alleviate the patients of its side effects without comprising the extent of pain relief.

The use of antagonist to address the potential side effects and the abuse are known in the art. Opioid antagonists are entities that modify the response of opioid receptors. Opioid antagonists include naloxone, naltrexone, diprenorphine, etorphine, dihydroetorphine, nalinefene, cyclazacine, levallorphan, pharmaceutically acceptable salts thereof and mixtures thereof.

For example, U.S. Pat. No. 5,866,164 describes a dosage system that comprises multiple layers with an opioid analgesic and the second layer comprises an antagonist for this opioid analgesic and simultaneously affecting the push function. U.S. Pat. No. 5,472,943 to Crain et al. describes methods of enhancing the analgesic potency of bimodally acting opioid agonists by administering the agonist with an opioid antagonist. U.S. Pat. No. 6,277,384 purported to provide a dosage form containing a combination of an opioid agonist and an opioid antagonist in a specific ratio, which brings about a negative effect on administration to an addicted person. U.S. Pat. No. 6,228,863 describes a dosage form containing a combination of an opioid agonist and an opioid antagonist, such that the two compounds can in each case only be extracted together from the dosage form and then additional processes required to separate them. U.S. Pat. No. 6,765,010 disclosures relate to compositions and methods with tramadol and an opioid antagonist to improve the efficacy of tramadol. U.S. Pat. Application No. 2005/0191244 describes the opioid agonist formulations comprising an opioid agonist, antagonist and gelling agent or an irritant to prevent the abuse opioid agonist. U.S. Pat. No. 6,716, 449 describes controlled release opioid agonist and controlled release opioid antagonist combinations for enhancing the analgesic potency of an opioid agonist and U.S. Pat. No. 7,332,142 describes pharmaceutical composition comprising an opioid agonist, an opioid antagonist and an irritant purport to lessen the abuse. U.S. Pat. No. 6,559,159 to Carroll et al. describes the use of kappa receptors antagonist for the treatment of opioid related addictions. U.S. Pat. No. 6,309,668 describes a tablet for oral administration containing two or more layers comprising one or more drugs and one or more gelling agents within separate layers of the tablet. U.S. Pat. No. 6,228,863 teaches the reduction of the abuse potential of oral dosage forms of opioid analgesics by selecting the particular opioid agonist and antagonist pair, and the concentrations of the same such that the antagonist cannot be easily extracted from the agonist. U.S. Pat. Nos. 6,277,384, 6,375,957 and 6,475,494 describe oral dosage forms including a combination of an orally active opioid agonist and an orally active opioid antagonist in a ratio that, when delivered orally, is analgesically effective but that is aversive in a physically dependent subject.

The prior art doesn't disclose a dosage form comprising at least one form of tapentadol and at least one opioid antagonist wherein the said tapentadol is in an optimal or suboptimal amount and the said antagonist is in amount effective to improve the efficacy and or reduce the side effects of tapentadol. Similarly, there is no report in the art of a method of treating pain by administering, to patient in need thereof, a dosage form comprising at least one form of tapentadol and at least one opioid antagonist wherein the said tapentadol is in an optimal or suboptimal amount and the said antagonist is in amount effective to improve the efficacy and or reduce the side effects of tapentadol. Similarly the prior art doesn't disclose a dosage form comprising at least one form of tapentadol and at least one opioid antagonist wherein the said tapentadol is in an optimal or suboptimal amount and the said antagonist is in amount effective to improve the efficacy and or reduce the side effects of tapentadol, such that the said dosage form provides effective pain relief for at least about 12 hours, or at least about 24 hours, when orally administered to a human patient.

Similarly, the prior art discloses neither a dosage form comprising at least one form of tapentadol and at least one opioid antagonist, and a therapeutically effective amount of a second analgesic wherein the said antagonist improves the efficacy and or reduces the side effects of tapentadol nor a method of treating pain and pain related conditions by administering to a patient in need thereof, a dosage forms comprising at least one form of tapentadol and at least one opioid antagonist wherein the said tapentadol is in an optimal or suboptimal amount and the said antagonist, and a therapeutically effective amount of a second drug wherein the said antagonist improves the efficacy and or reduces the side effects of tapentadol. The second analgesic is selected from a group consisting of an NSAID, Acetaminophen, a GABA analogue, a Serotonin Norepinephrine reuptake inhibitor (SNRI), a Cyclo-oxygenase-(COX)-inhibiting nitric oxide donator, a HT Agonist and a Proton Pump Inhibitor., tramadol, hydromorphone, faxeladol, axomadol, oxycodone, hydrocodone, fentanyl, morphine, pharmaceutically acceptable salts thereof and mixtures thereof.

BRIEF DESCRIPTION OF THE INVENTION

The objects of the present invention are directed to provide dosage forms comprising at least one form of tapentadol and at least one antagonist and to methods for improving the efficacy of tapentadol and/or minimizing its adverse effects in a human. The compositions and methods of the present invention include immediate release and slow release dosage forms of at least one form of tapentadol and at least one opioid antagonist wherein the said tapentadol is in an optimal or suboptimal amount. The dosage forms include those comprising at least one form of tapentadol, at least one opioid agonist and a therapeutically effective amount of a second analgesic wherein the said antagonist improves the efficacy and or reduces the side effects of tapentadol.

One object of the present invention is to provide dosage form comprising at least one form of tapentadol and at least one opioid antagonist, wherein the said tapentadol is in an optimal or suboptimal amount and the said antagonist is present in an amount to improve the efficacy and or reduce the side effects of tapentadol.

One object of the present invention is to provide a method of treating pain by administering dosage form comprising at least one form of tapentadol and at least one opioid antagonist wherein the said tapentadol is in an optimal or suboptimal amount and the said antagonist is present in an amount to improve the efficacy and or reduces the side effects of tapentadol.

One object of the present invention is to provide a dosage form comprising at least one form of tapentadol and at least one opioid antagonist wherein the said dosage form provides effective pain relief for at least about 12 hours, when administered to a human patient.

One object of the present invention is to provide a method of treating pain by administering a dosage form comprising at least one form of tapentadol and at least one opioid antagonist wherein the said dosage form provides effective pain relief for at least 12 hours, when administered to a human patient.

One object of the present invention is to provide dosage form comprising at least one form of tapentadol and at least one opioid antagonist wherein the said dosage form provides effective pain relief for at about 24 hours, when administered to a human patient.

One object of the present invention is to provide a method of treating pain by administering a dosage form comprising at least one form of tapentadol and at least one opioid antagonist wherein the said dosage form provides effective pain relief for about 24 hours, when administered to a human patient.

Still further, the present invention provides a method for improving the efficacy of at least form of tapentadol in a human subject by administering to the human subject at least form of tapentadol and at least one opioid antagonist effective to improve the efficacy of at least form of tapentadol, wherein the said tapentadol is in an optimal or suboptimal amount. Preferred opioid antagonists include naltrexone, naloxone, or nalmefene. The efficacy of at least one form of tapentadol may be maintained while one or more side effects are minimized without increasing or decreasing the cumulative daily dose of tapentadol.

Yet another object of the present invention is to provide a method for minimizing an adverse side effect associated with the administration of at least form of tapentadol to a human subject by administering to the human subject at least form of tapentadol and at least one opioid antagonist wherein the said tapentadol is in an optimal or suboptimal amount and the said antagonist is in amount effective to minimize an adverse side effect. Adverse side effects include, but are not limited to, nausea, vomiting, dizziness, headache, somnolence or pruritis.

The present invention further provides a method for treating pain in a human subject by administering to the human subject at least form of tapentadol, a second analgesic, at least one opioid antagonist effective to improve the efficacy of tapentadol, as well as a method for treating pain with at least form of tapentadol and minimizing an adverse side effect of tapentadol in a human subject by administering to the human subject at least one form of tapentadol, a second analgesic, and at least one opioid antagonist wherein the said tapentadol is in an optimal or suboptimal amount and the said antagonist is present in amount effective to minimize an adverse side effect.

One object of the present invention is to provide dosage form comprising at least one form of tapentadol, at least one opioid antagonist and a second analgesic wherein the said tapentadol is in an optimal or suboptimal amount and the said antagonist improves the efficacy and or reduces the side effects of tapentadol.

One object of the present invention is to provide a method of treating pain by administering dosage form comprising at least one form of tapentadol, at least one opioid antagonist and a second analgesic wherein the said tapentadol is in an optimal or suboptimal amount and the said antagonist improves the efficacy and or reduces the side effects of tapentadol.

One object of the present invention is to provide dosage form comprising at least one form of tapentadol, at least one opioid antagonist and a second analgesic wherein the said dosage form provides effective pain relief for at least about 12 hours, when administered to a human patient.

One object of the present invention is to provide a method of treating pain by administering a dosage form comprising at least one form of tapentadol, at least one opioid antagonist and a second analgesic, wherein the said dosage form provides effective pain relief for at least 12 hours, when administered to a human patient.

One object of the present invention is to provide dosage form comprising at least one form of tapentadol, at least one opioid antagonist and a second analgesic analgesic, wherein the said dosage form provides effective pain relief for at about 24 hours, when administered to a human patient.

One object of the present invention is to provide a method of treating pain by administering a dosage form comprising at least one form of tapentadol, at least one opioid antagonist and a second analgesic, wherein the said dosage form provides effective pain relief for about 24 hours, when administered to a human patient.

Still further, the present invention provides a method for improving the efficacy of at least form of tapentadol in a human subject by administering to the human subject a dosage form comprising at least one form of tapentadol, at least one opioid antagonist and a second analgesic, wherein the said tapentadol is in an optimal or suboptimal amount. Preferred opioid antagonists include naltrexone, naloxone, or nalmefene. The efficacy of at least one form of tapentadol may be maintained while one or more side effects are minimized without increasing or decreasing the cumulative daily dose of tapentadol.

Yet another object of the present invention is to provide a method for minimizing an adverse side effect associated with the administration of at least form of tapentadol to a human subject by administering to the human subject a dosage form comprising at least one form of tapentadol, at least one opioid antagonist and a second analgesic, wherein the said tapentadol is in an optimal or suboptimal amount and the said antagonist is in amount effective to minimize an adverse side effect. Adverse side effects include, but are not limited to, nausea, vomiting, dizziness, headache, somnolence or pruritis.

Another object of the present invention is to provide a dosage form comprising at least one form of tapentadol, at least one opioid antagonist and a second analgesic, wherein the dosage form, upon oral administration, results in an adverse event profile which is better than the adverse event profile resulting from the administration of a dosage form without an opioid antagonist.

Still further the present inventions provides a dosage form and methods for enhancing analgesic potency of tapentadol in combination with an opioid antagonist, and at least one additional drug, and/or minimizing its adverse effects, particularly its adverse side effects in humans, wherein one of the active agents is in slow release form. Principle adverse side effects of tapentadol in humans include dizziness, nausea, constipation, headache, somnolence, vomiting, pruritis, CNS stimulation, seizures, asthenia, dyspepsia, diarrhea, dry mouth and/or sweating.

In certain preferred embodiments, the second drug is selected from the group consisting of NSAID, Acetaminophen, a GABA analogue, a Serotonin Norepinephrine reuptake inhibitor (SNRI), a Cyclo-oxygenase-(COX)-inhibiting nitric oxide donator, a HT Agonist and a Proton Pump Inhibitor., tramadol, hydromorphone, faxeladol, axomadol, oxycodone, hydrocodone, fentanyl, morphine, pharmaceutically acceptable salts thereof and mixtures thereof. In certain preferred embodiments, the opioid antagonist is selected from the group consisting of naltrexone, naloxone, nalmefene, pharmaceutically acceptable salt thereof or a combination thereof.

In certain embodiments of the present invention, the dosage form comprises at least one form of tapentadol and at least one opioid antagonist wherein the dosage form is a transdermal delivery system, an oral mucosal delivery system, a dosage form suitable for intranasal administration, a buccal delivery system, an injectable dosage form, and a solid oral dosage form.

In another embodiment of this invention, the dosage forms include but not limited to granules, spheroids, pellets, multiparticulates, aerosols, capsules, patches, tablets, sachets, controlled release suspensions, or in any other suitable dosage form incorporating such granules, spheroids, pellets or multiparticulates.

ILLUSTRATION OF FIGURES

The invention is illustrated by the following figures. The figures shown are for illustrative purposes and they do not limit the scope of the invention.

FIG. 4 shows comparison of key side effects associated with Tapentadol 50 mg with Naloxone (0.1 mg), with Naltrexone (0.1 mg), and with Nalmefene (0.1 mg).

FIG. 5 represents the 4-hour Total Pain Relief Scores (TOTPAR) for slow release tapentadol 100 mg with Naloxone (0.1 mg), with Naltrexone (0.1 mg), and with Nalmefene (0.1 mg) and fixed dose combination of slow release tapentadol 100 mg and Naltrexone 1 mg.

FIG. 6 represents the hourly pain relief scores from 0-12, 0-8 and 0-4 hours for for slow release tapentadol 100 mg with Naloxone (0.1 mg), with Naltrexone (0.1 mg), and with Nalmefene (0.1 mg) and fixed dose combination of slow release tapentadol 100 mg and Naltrexone 1 mg.

FIG. 7 represents Changes in the Δ mean pain relief scores at four hours and at eight hours and twelve hours for for slow release tapentadol 100 mg with Naloxone (0.1 mg), with Naltrexone (0.1 mg), and with Nalmefene (0.1 mg) and fixed dose combination of slow release tapentadol 100 mg and Naltrexone 1 mg.

FIG. 8 shows comparison of key side effects associated with for slow release tapentadol 100 mg with Naloxone (0.1 mg), with Naltrexone (0.1 mg), and with Nalmefene (0.1 mg) and fixed dose combination of slow release tapentadol 100 mg and Naltrexone 1 mg.

Figure 9:
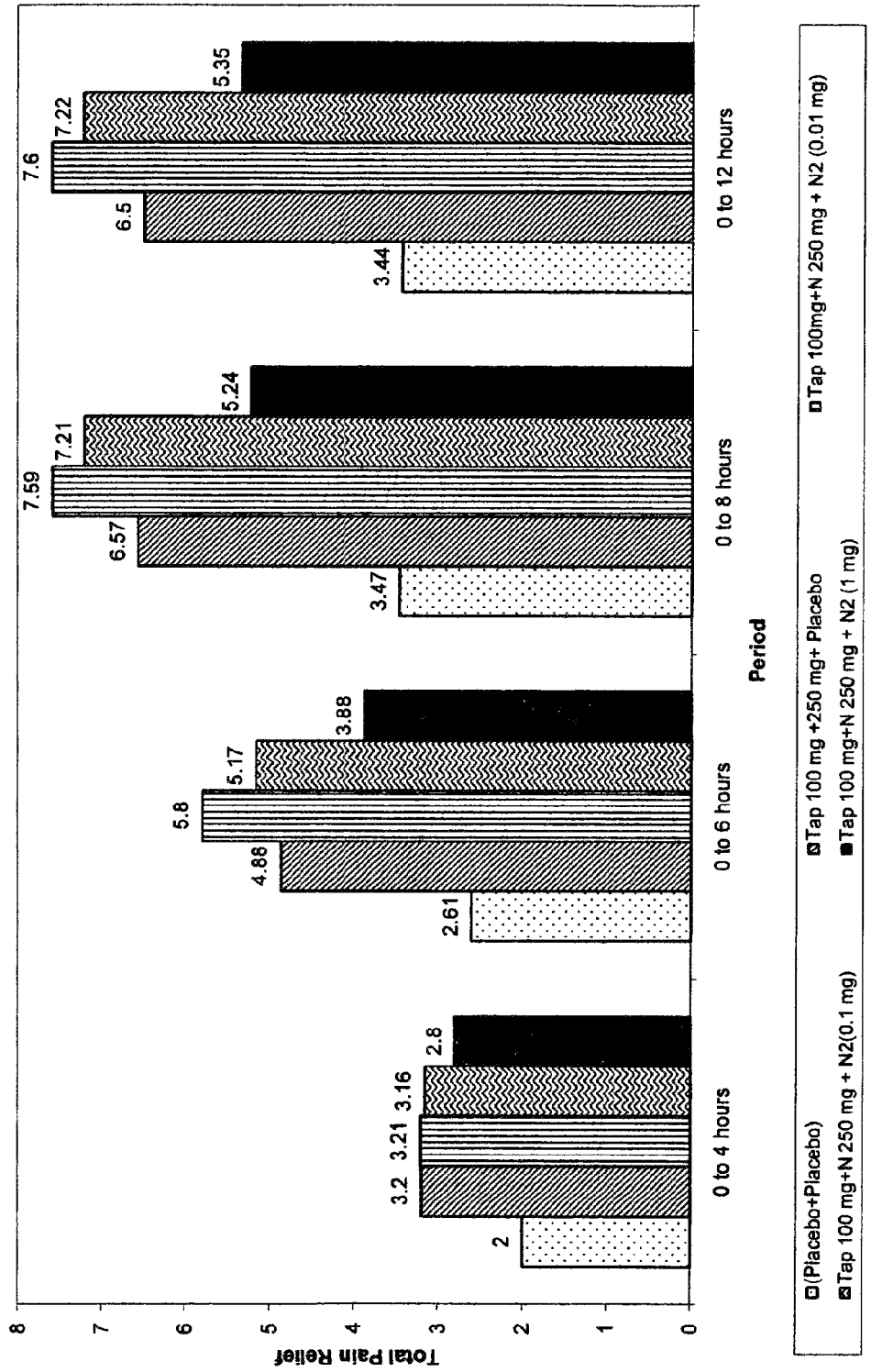

FIG. 9 represents the 4-hour Total Pain Relief Scores (TOTPAR) for Tapentadol 100 mg+Naproxen 250 mg with Naltrexone.

Figure 10:
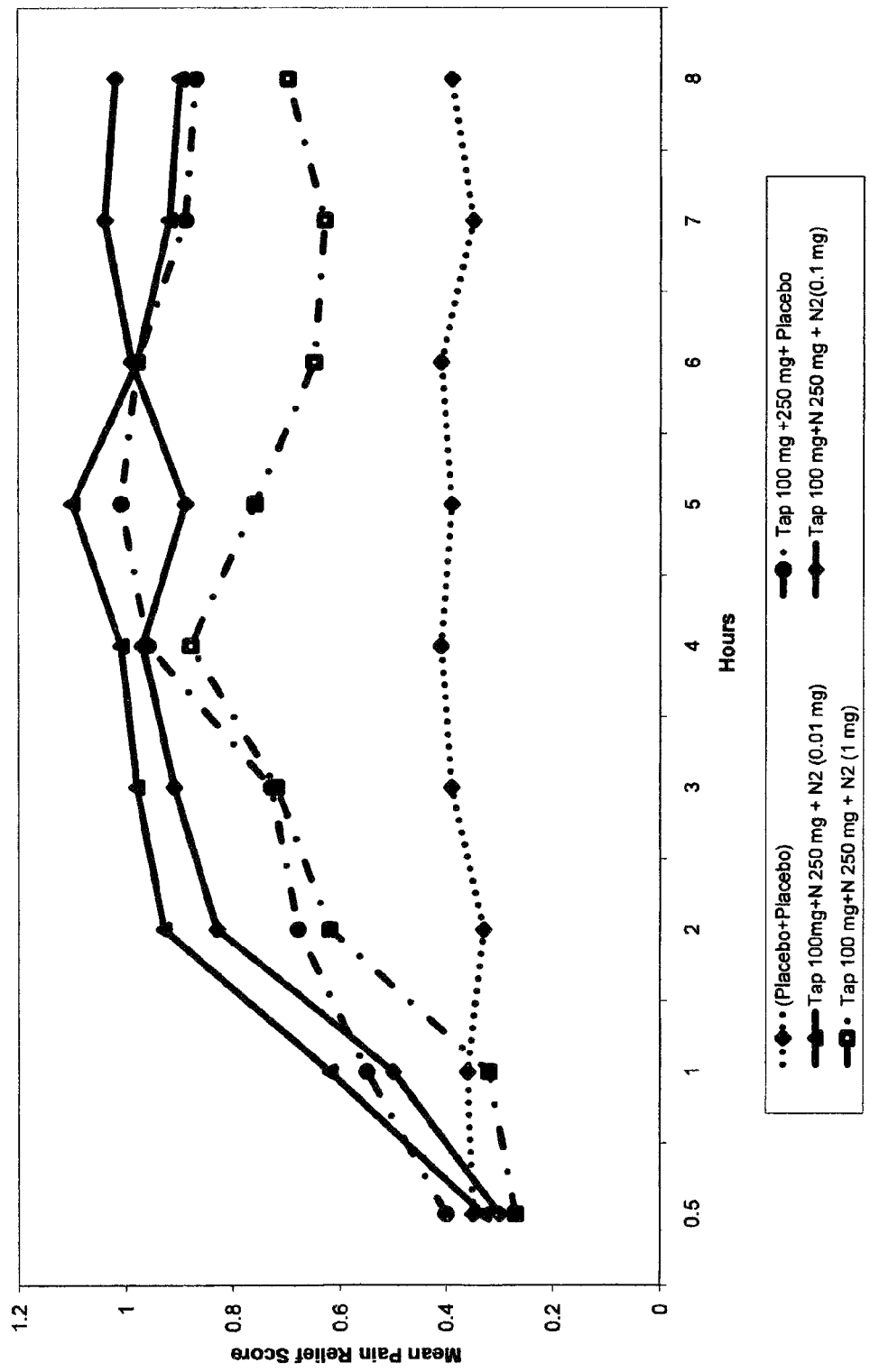

FIG. 10 represents the hourly pain relief scores from 0-12, 0-8 and 0-4 hours for Tapentadol 100 mg+Naproxen 250 mg with Naltrexone.

Figure 11:
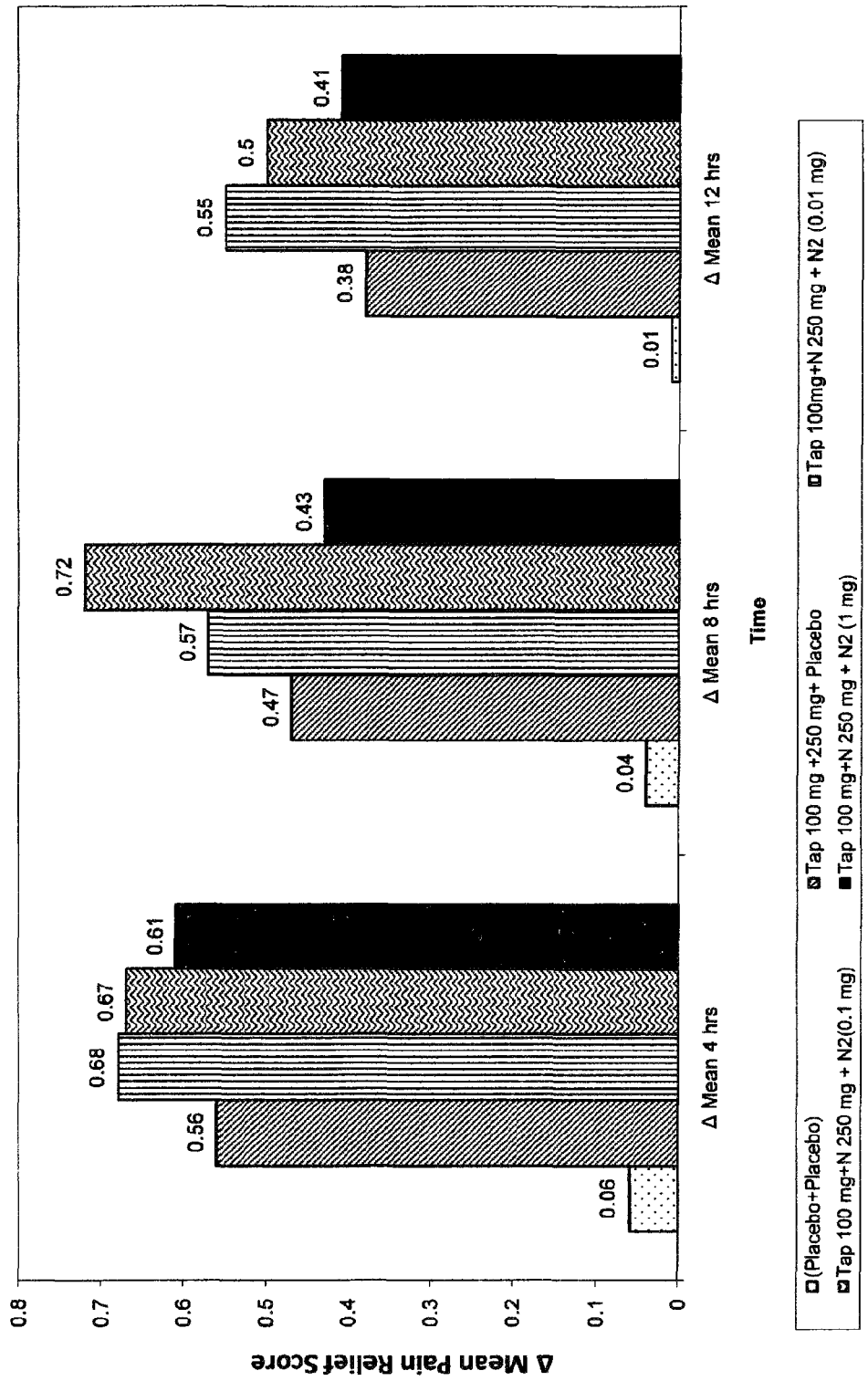

FIG. 11 represents the changes in the Δ mean pain relief scores at four hours and at eight hours and twelve for Tapentadol 100 mg+Naproxen 250 mg with Naltrexone.

Figure 12:
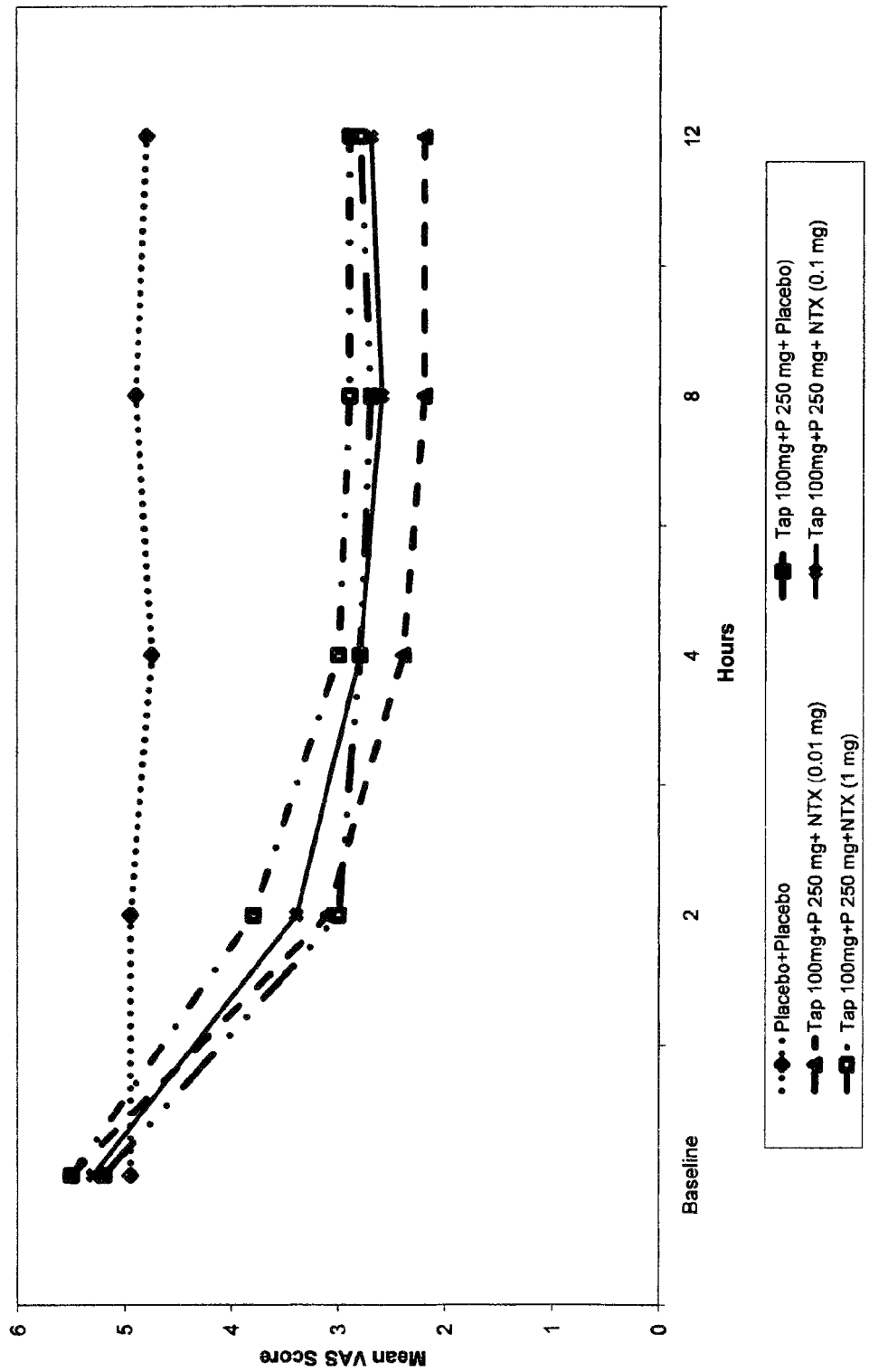

FIG. 12 shows the mean VAS pain score changes for Tapentadol 100 mg+Pregabalin 250 mg with Naltrexone.

Figure 13:
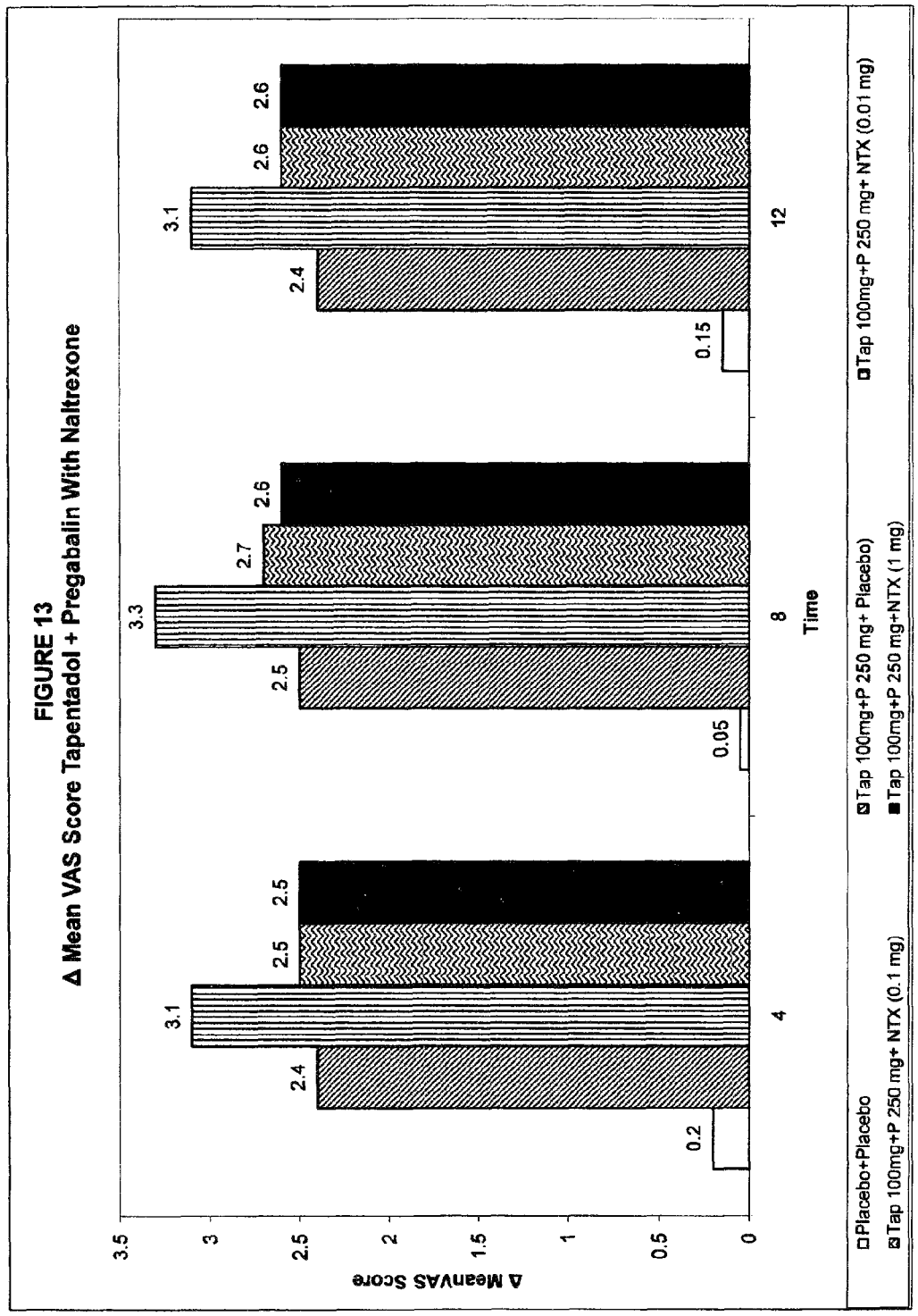

FIG. 13 shows the Δ mean VAS pain score changes in VAS pain for Tapentadol 100 mg+Pregabalin 250 mg with Naltrexone.

Figure 14:
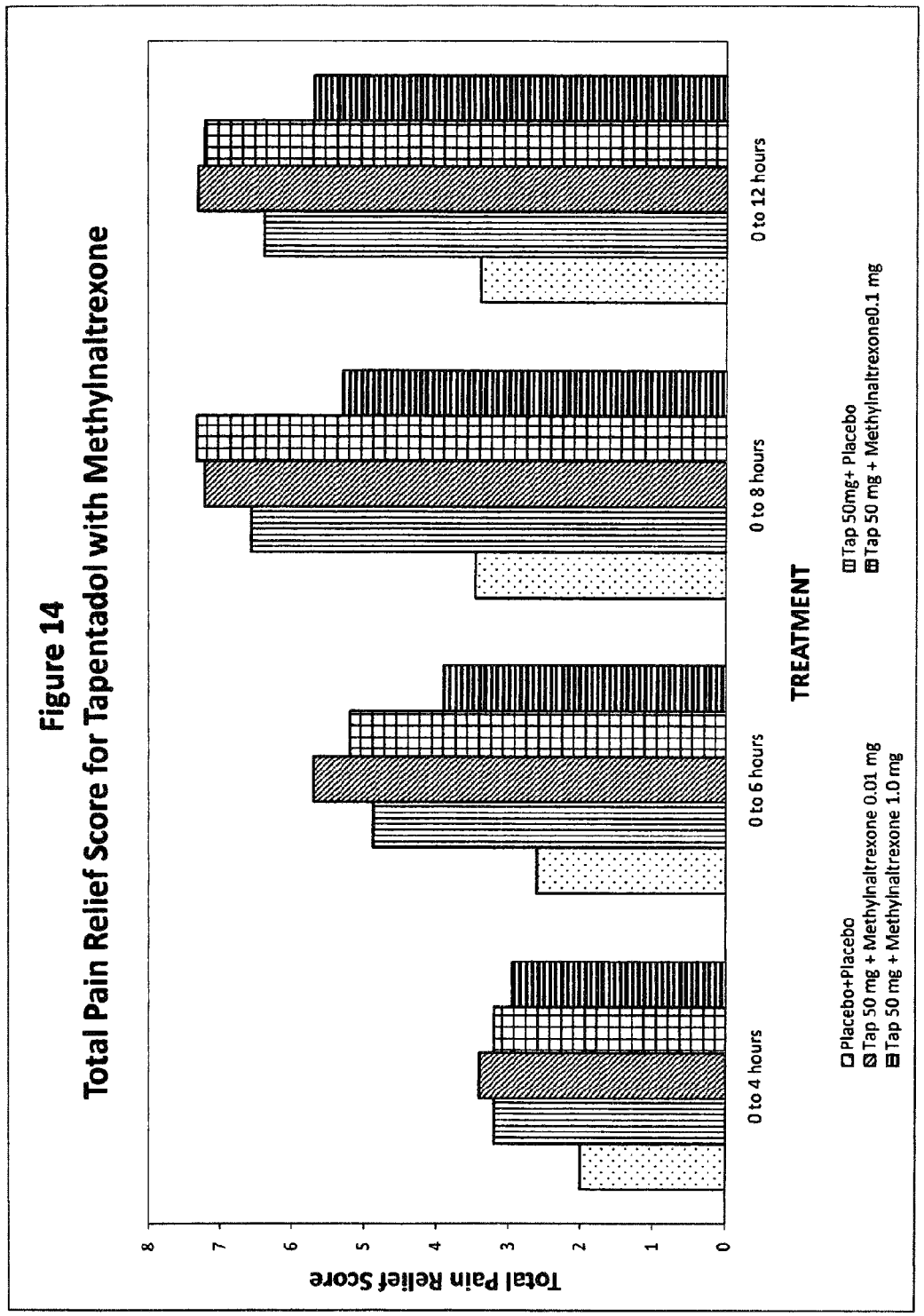

FIG. 14 represents the 4-hour Total Pain Relief Scores (TOTPAR) for Tapentadol (50 mg) with Methylnaltrexone (0.01 mg), with Methylnaltrexone (0.1 mg), and with Methylnaltrexone (1 mg).

Figure 15:
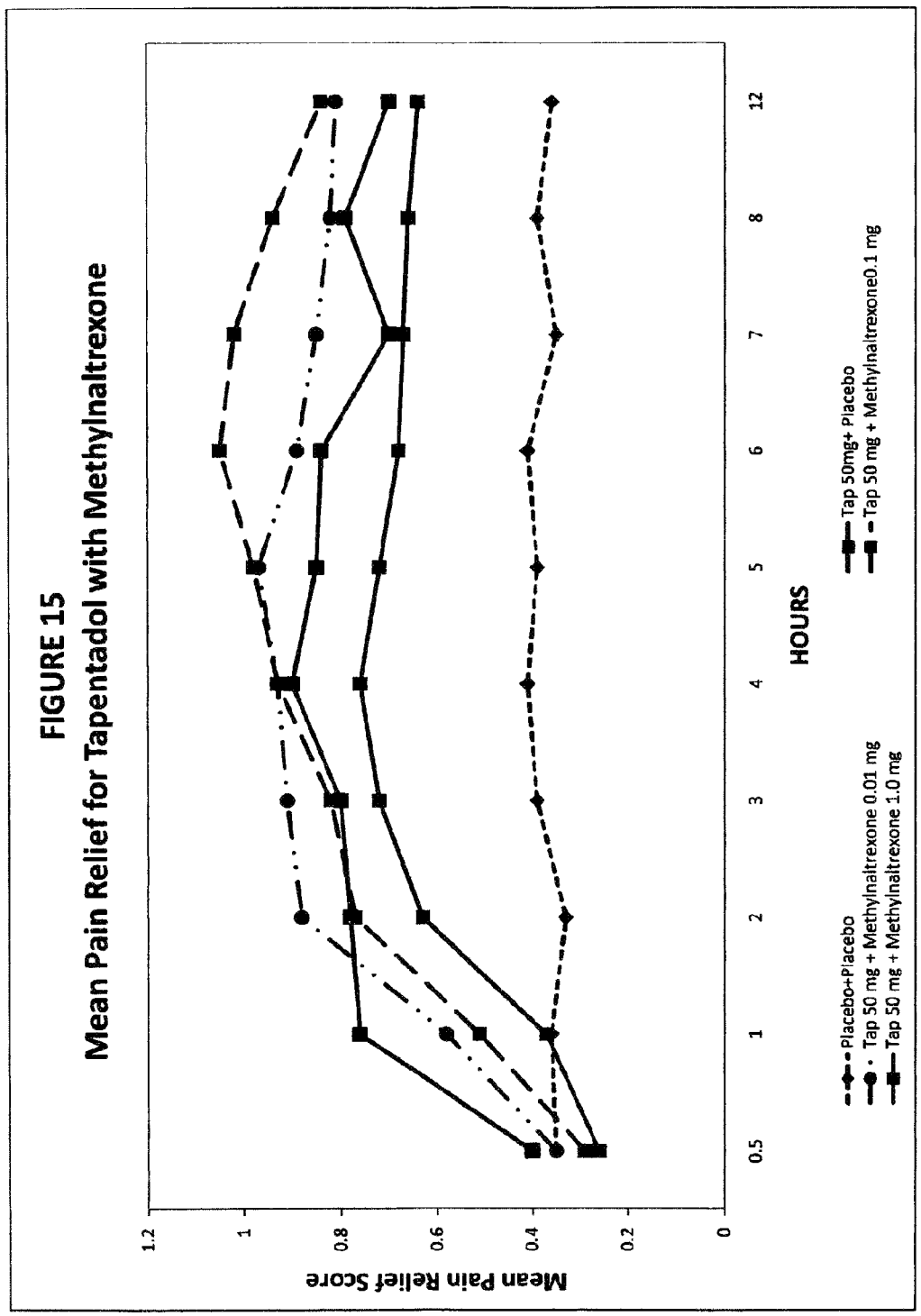

FIG. 15 represents the hourly pain relief scores from 0-12, 0-8 and 0-4 hours for Tapentadol (50 mg) with Methylnaltrexone (0.01 mg), with Methylnaltrexone (0.1 mg), and with Methylnaltrexone (1 mg).

Figure 16:
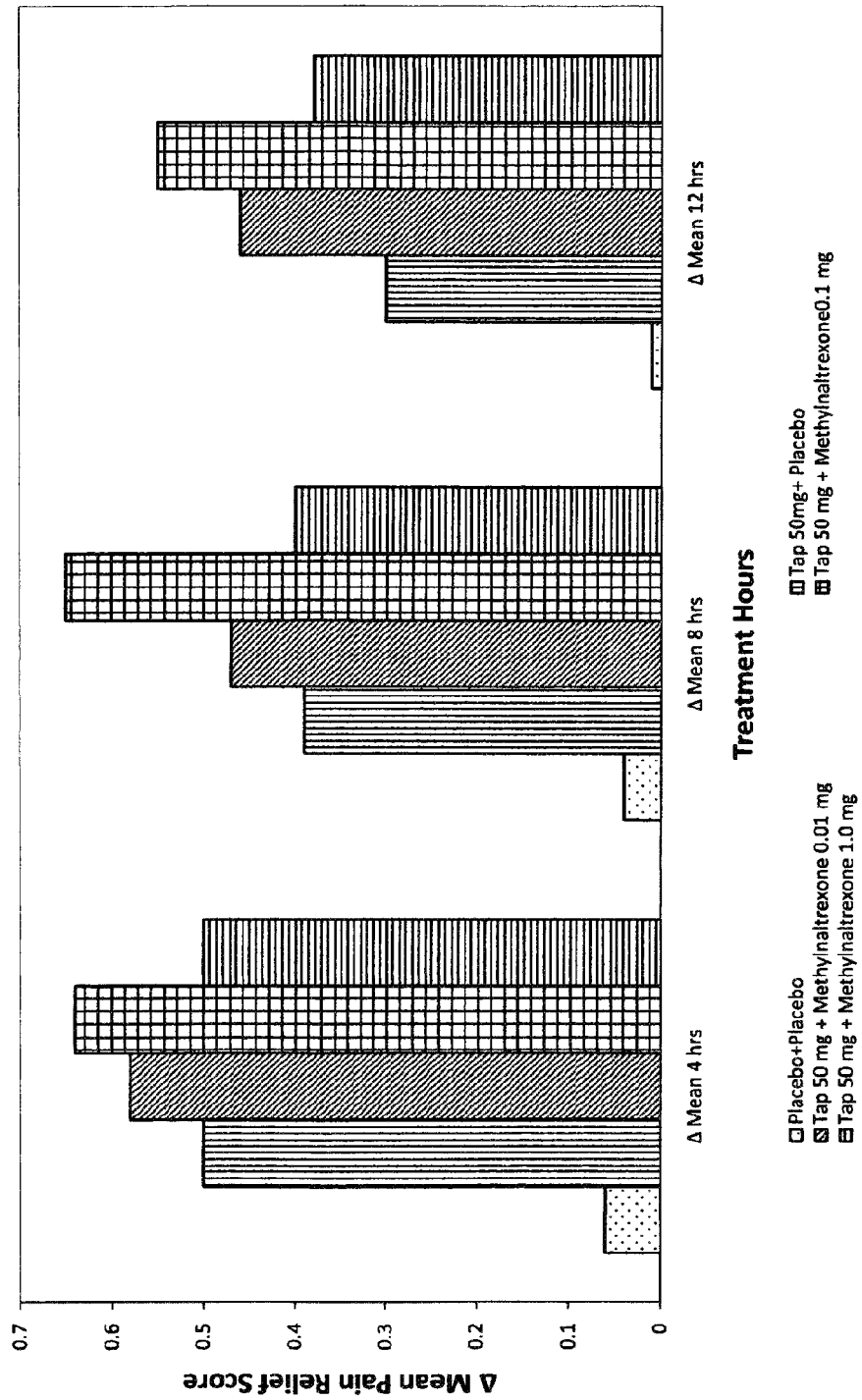

FIG. 16 represents Changes in the Δ mean pain relief scores at four hours, at eight hours and twelve hours for Tapentadol (50 mg) with Methylnaltrexone (0.01 mg), with Methylnaltrexone (0.1 mg), and with Methylnaltrexone (1 mg).

FIG. 17 shows comparison of the extent of constipation associated with Tapentadol (50 mg) with Methylnaltrexone (0.01 mg), with Methylnaltrexone (0.1 mg), and with Methylnaltrexone (1 mg).

DETAILED DESCRIPTION OF THE INVENTION

The terms "second drug" or "second analgesic" as used in this invention means to include any drug used to relieve pain drug is selected from the group consisting of NSAID, Acetaminophen, a GABA analogue, a Serotonin Norepinephrine reuptake inhibitor (SNRI), a Cyclo-oxygenase- (COX)-inhibiting nitric oxide donator, a HT Agonist and a Proton Pump Inhibitor., tramadol, hydromorphone, faxeladol, axomadol, oxycodone, hydrocodone, fentanyl, morphine, pharmaceutically acceptable salts thereof and mixtures thereof and various others other classes of drugs not normally considered analgesics are used to treat neuropathic pain syndromes; these include tricyclic antidepressants and anticonvulsants The term "band range" for purposes of the present invention is defined as the difference in vitro dissolution measurements of the controlled release formulations when comparing the dissolution profile (curve) obtained by the formulation upon completion of the manufacturing of the coated product (prior to storage) and the dissolution profile obtained after the coated product is exposed to accelerated storage conditions, expressed as the change in percent of the active agent released from the coated product at any dissolution time point along the dissolution curves.

The term "antianalgesia" as used herein means is the ability of some endogenous response to counter the effects of exogenous analgesic drug.

The term "hyperexcitability" as used herein means the state or condition of being unusually or excessively excitable effects of a drug The term "physical dependence" as used herein means refers to a state resulting from chronic use of a drug The term "tolerance" as used herein means physiological tolerance or drug tolerance is commonly encountered when a subject is treated with a drug.

The term "improving" as used herein means enhancing, supporting, advancing and furthering, say efficacy.

The term "reducing" as used herein means attenuating, blocking, inhibiting and preventing say a side effect.

The term "co-administration" as used herein means administration of the two compounds to the patient within a period of 24 hours. The term includes separate administration of two medicaments each containing one of the compounds as well as simultaneous administration whether or not the two compounds are combined in one formulation or whether they are in two separate formulations.

The term "opioid agonist or opioid agonists" as used herein mean any entity that brings out biological response by acting on an opioid receptors. These include but not limited to opioid agonists useful in the present invention include, but are not limited to, alfentanil, allylprodine, alphaprodine, anileridine, axomadol, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tapentadol, axamadol, and, tramadol, mixtures or salts of any of the foregoing,.

The term "bimodally-acting opioid agonists" is used for opioid agonists that bind to and activate both inhibitory and excitatory opioid receptors on nociceptive neurons which mediate pain. Activation of inhibitory receptors by said agonists causes analgesia. Activation of excitatory receptors by said agonists results in anti-analgesia, hyperexcitability, hyperalgesia, as well as development of physical dependence, tolerance and other undesirable side effects.

The term "excitatory opioid receptor antagonists" is used for opioids which bind to and act as antagonists to excitatory but not inhibitory opioid receptors on nociceptive neurons which mediate pain. That is, excitatory opioid receptor antagonists are compounds which bind to excitatory opioid receptors and selectively block excitatory opioid receptor functions of nociceptive types of DRG neurons at 1,000 to 10,000-fold lower concentrations than are required to block inhibitory opioid receptor functions in these neurons.

The term "dosage form" as used herein is defined to mean a pharmaceutical preparation or system in which doses of medicine or active drug are included. A dosage form will desirably comprise, for example, an immediate release dosage form or one slow release dosage form including various slow release forms such as, osmosis controlled-release dosage form, erosion controlled-release dosage form, dissolution controlled-release dosage form, diffusion controlled-release dosage form, controlled-release matrix core, controlled-release matrix core coated with at least one release-slowing coat, enteric coated dosage form, one sustained dosage, dosage form surrounded by at least one delayed-release coat, capsules, minitablets, caplets, uncoated microparticles, microparticles coated with release-slowing coat, microparticles coated with delayed-release coat or any combination thereof. Within the context of this application, the dosage forms described herein mean a dosage form as defined above comprising an effective amount of tapentadol for treating a patient in need of.

The term "suboptimal dosage" us used herein means a dosage which is below the optimal dosage for that compound when used in single-compound therapy.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term "osmotic dosage form", "osmotic delivery device", "controlled-release osmotic dosage form" or "osmosis-controlled extended-release systems" as used herein is defined to mean dosage forms which forcibly dispense tapentadol all or in part by pressure created by osmosis or diffusion of fluid into a core which forces tapentadol to be dispensed from the osmotic dosage form. The term "osmotic dosage form", "osmotic delivery device" or "controlled-release osmotic dosage form" also encompasses such forms that will desirably be coated with at least one "release-slowing coat.

The term "prevention of a disease" as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term "pain and pain related conditions" as used herein is defined as any pain due to a medical conditions including neuropathic pain, osteoarthritis, rheumatoid arthritis, fibromyalgia, and back, musculoskeletal pain, Ankylosing spondylitis, juvenile rheumatoid arthritis, migraines, dental pain, abdominal pains, ischemic pain, postoperative pain or because of an anesthetic or surgical condition The term "extended release material" as present in the inner solid particulate phase and the outer solid continuous phase refers to one or more hydrophilic polymers and/or one or more hydrophobic polymers and/or one or more other type hydrophobic materials, such as, for example, one or more waxes, fatty alcohols and/or fatty acid esters. The "extended release material" present in the inner solid particulate phase may be the same as or different from the "extended release material" present in the outer solid continuous phase.

The term "Proton Pump Inhibitor" as used herein means any active agent that blocks hydrogen/potassium adenosine triphosphatase enzyme system (the H+/K+ ATPase,) of the gastric parietal cell including Omeprazole, Lansoprazole, Esomeprazole, Pantoprazole and Rabeprazole The term "5-HT agonists" as used herein means drugs that act on 5-HT receptor including sumatriptan, rizatriptan, zolmitriptan, almotriptan and frovatriptan.

The term "slow-release" here applies to any release from a formulation that is other than an immediate release wherein the release of the active ingredient is slow in nature. This includes various terms used interchangeably in the pharmaceutical context like extended release, delayed release, sustained release, controlled release, timed release, specific release, prolonged release and targeted release etc.

An "immediate release" coat, as used herein, is defined to mean a coat, which has substantially or appreciably no influence on the rate of release of tapentadol from the dosage form in-vitro or in-vivo. The excipients comprising the immediate release coat have no substantial controlled-release, swelling, erosion, dissolution, or erosion and swelling properties, which means that the composition of the coat has no substantial influence on the rate of release of the tapentadol.

The term "controlled-release" as used herein is defined to mean a substantially gradual rate of release of the drug in the first once daily controlled-release dosage form or the at least one means for controllably releasing the in a substantially controlled manner per unit time in-vivo. The rate of release of the drug is controlled by features of the dosage form and/or in combination with physiologic or environmental conditions rather than by physiologic or environmental conditions alone.

The term "controlled-release dosage forms" or dosage forms which exhibit a "controlled-release" of tapentadol as used herein is defined to mean dosage forms administered once daily that release drug at a relatively constant rate and provide plasma concentrations of the active drug that remain substantially invariant with time within the therapeutic range of the active drug over about a 24-hour period.

The term "sustained-release dosage forms" or dosage forms which exhibit a "sustained-release" of the drug as used herein is defined to mean dosage forms administered once daily that provide a release of the drug sufficient to provide a therapeutic dose after administration, and then a gradual release over an extended period of time such that the sustained-release dosage form provides therapeutic benefit over a 24-hour period.

The term "extended-release dosage forms" or dosage forms which exhibit an "extended release" of drug as used herein is defined to mean dosage forms administered once daily that release drug slowly, so that plasma concentrations of the drug are maintained at a therapeutic level for an extended period of time such that the sustained-release dosage form provides therapeutic benefit over a 24-hour period.

The term "multiparticulate" or "microparticle" as used herein is defined to mean a plurality of drug-containing units, such as for example microspheres, spherical particles, microcapsules, particles, microparticles, granules, spheroids, beads, pellets, or spherules.

The term "prolonged-release dosage forms" or dosage forms which exhibit a "prolonged release" of the drug as used herein is defined to mean dosage forms administered once daily which provide for absorption of the drug over a longer period of time than from an immediate-release dosage form and which provide therapeutic benefit over a 24-hour period.

The term "bioequivalence" is defined as there being about a 90% or greater probability that the bioavailability (AUC) of tapentadol as determined by standard methods is about 80 to about 125% of the second orally administrable dosage form comprising the same dose of tapentadol and that there is a about 90% or greater probability that the maximum blood plasma concentration ($C_{max}$) of tapentadol as measured by standard methods is about 80 to about 125% of the second orally administrable dosage form.

The term "FDA guidelines" refers to the guidance, Guidance for Industry Bioavailability and Bioequivalence Studies approved by the US Food and Drug Administration at the time of filing of this patent application.

The term "candidate for sustained release" encompasses all the characteristics of a drug which make it a candidate for formulating it into an extended release fashion like a short elimination half life and consequent dosing of more than once a day, a single dose product given in an extended fashion to achieve better clinical results and avoid side effects associated with an immediate release etc.

The term "delayed-release dosage forms" or dosage forms which exhibit a "delayed-release" of the drug as used herein is defined to mean dosage forms administered once daily that do not substantially release drug immediately following administration but at a later time. Delayed-release dosage forms provide a time delay prior to the commencement of drug-absorption. Such dosage forms will desirably be coated with a delayed-release coat. This time delay is referred to as "lag time" is different from term "onset time" which represents latency, that is, the time required for the drug to reach a minimum effective concentration.

The term "dose dumping" as used herein is defined to mean the unintended fluctuation of drug release, e.g., the rapid drug release of drug in a short period of time irrespective of the cause.

"enhanced absorption dosage forms" or dosage forms which exhibit an "enhanced absorption" of the drug as used herein is defined to mean dosage forms that when exposed to like conditions, will show higher release and/or higher absorption of the drug as compared to other dosage forms with the same or higher amount of drug.

The term "binding agent" as used in this specification, refers to any conventionally known pharmaceutically acceptable binder such as polyvinyl pyrrolidone, hydroxypropyl cellulose, hydroxyethyl cellulose, hydroxypropyl methylcellulose, ethylcellulose, polymethacrylate, polyvinylalcohol, waxes and the like. Mixtures of the aforementioned binding agents may also be used. The preferred binding agents are water soluble materials such as polyvinyl pyrrolidone having a weight average molecular weight of 25,000 to 3,000,000. The binding agent may comprise approximately about 0 to about 40% of the total weight of the core and preferably about 3% to about 15% of the total weight of the core. In one embodiment, the use of a binding agent in the core is optional.

The term "pharmaceutically acceptable derivative" means various pharmaceutical equivalent isomers, enantiomers, salts, hydrates, polymorphs, esters etc of tapentadol.

The term "modified-release dosage forms" or dosage forms which exhibit a "modified-release" of the drug as used herein is defined to mean dosage forms whose drug release characteristics of time course and/or location are designed to accomplish therapeutic or convenience objectives not offered by an immediate-release dosage forms. Modified-release dosage forms or dosage forms are typically designed to provide a quick increase in the plasma concentration of the drug which remains substantially constant within the therapeutic range of the drug for at least a 24-hour period. Alternatively, modified-release dosage forms will desirably be designed to provide a quick increase in the plasma concentration of the drug, which although may not remain constant, declines at rate such that the plasma concentration remains within the therapeutic range for at least a 24-hour period.

The term "therapeutically effective amount" means an amount that elicits a biological response in a mammal including the suboptimal amount.

The term "hydrophilic polymers" as used in this specification include, but are not limited to hydroxypropylmethylcellulose, hydroxypropylcellulose, sodium, carboxymethyl-cellulose, carboxymethylcellulose calcium, ammonium alginate, sodium alginate, potassium alginate, calcium alginate, propylene glycol alginate, alginic acid, polyvinylalcohol, povidone, carbomer, potassium pectate, potassium pectinate, etc The term " hydrophobic polymers" as used in this specification include, but are not limited, to ethyl cellulose, hydroxyethylcellulose, ammonio methacrylate copolymer (Eudragit RL™ or Eudragit RS™), methacrylic acid copolymers (Eudragit L™ or Eudragit S™) methacrylic acid-acrylic acid ethyl ester copolymer (Eudragit L 100-5™), methacrylic acid esters neutral copolymer (Eudragit NE 30D™), dimethylaminoethylmethacrylate-methacrylic acid esters copolymer (Eudragit E 100™), vinyl methyl ether/malefic anhydride copolymers, their salts and esters (Gantrez™) etc.

"Tapentadol" as used herein is defined to mean at least one form of tapentadol chosen from tapentadol base, the individually optically active enantiomers of tapentadol, such as for example, (+) or (−) forms of tapentadol, racemic mixtures thereof, active metabolites, pharmaceutically acceptable salts thereof, such as for example, acid addition or base addition salts of tapentadol. Acids commonly employed to form acid addition salts are inorganic acids, such as for example, hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutylate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutylate, citrate, lactate, g-hydroxybutylate, glycolate, tartrate, methanesulfonate, propanesulfonate, naphthalene-1-sulfonate, napthhalene-2-sulfonate, mandelate and the like. Base addition salts include those derived from inorganic bases, such as for example, ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

An "immediate release coat", as used herein, is defined to mean a coat, which has substantially or appreciably no influence on the rate of release of the drug from the dosage form in-vitro or in-vivo. The excipients comprising the immediate release coat have no substantial controlled-release, swelling, erosion, dissolution, or erosion and swelling properties, which means that the composition of the coat has no substantial influence on the rate of release of the drug.

The term "osmotic dosage form", "osmotic delivery device", "controlled-release osmotic dosage form" or "osmosis-controlled extended-release systems" as used herein is defined to mean dosage forms which forcibly dispense the drug all or in part by pressure created by osmosis or diffusion of fluid into a core which forces the drug to be dispensed from the osmotic dosage form. The term "osmotic dosage form", "osmotic delivery device" or "controlled-release osmotic dosage form" also encompasses such forms that will desirably be coated with at least one "release-slowing coat.

Other hydrophobic materials which may be employed in the inner solid particulate phase and/or outer solid continuous phase include, but are not limited to, waxes such as beeswax, carnauba wax, microcrystalline wax, and ozokerite; fatty alcohols such as cetostearyl alcohol, stearyl alcohol; cetyl alcohol myristyl alcohol etc; and fatty acid esters such as glyceryl monostearate, glycerol monooleate, acetylated monoglycerides, tristearin, tripalmitin, cetyl esters wax, glyceryl palmitostearate, glyceryl behenate, hydrogenated castor oil, etc.

The present invention provides an oral dosage form comprising at least one form of tapentadol, and at least one antagonist, wherein the said antagonist improves the efficacy of the said opioid agonist and reduces the adverse side effects of the said opioid agonist. This is achieved by placing one or more antagonist of tapentadol within the dosage formulation of the active agent pharmaceutical product so that the said antagonist is bioavailable just enough to improve the efficacy of tapentadol.

The instant oral dosage forms comprises an optimal or suboptimal amount of at least one form of tapentadol, and at least one antagonist, wherein the said antagonist improves the efficacy of tapentadol and reduces the adverse side effects of tapentadol, and the said dosage form provides effective clinical relief for at least about 12 hours when administered to a human patient.

The instant oral dosage forms comprises an optimal or suboptimal amount of at least one form of tapentadol, and at least one antagonist, wherein the said antagonist improves the efficacy of tapentadol and reduces the adverse side effects of tapentadol, and the said dosage form provides effective clinical relief for up to about 24 hours when administered to a human patient.

The present invention provides a method of administering an oral dosage form comprising an optimal or suboptimal amount of at least one form of tapentadol, and at least one antagonist, wherein the said antagonist improves the efficacy of tapentadol and reduces the adverse side effects of tapentadol. This is achieved by placing one or more antagonist of tapentadol within the dosage formulation or co-administered with tapentadol and or a second analgesic so that the said antagonist is bioavailable just enough to improve the efficacy of tapentadol.

The present invention provides a method of administering an oral dosage form comprising an optimal or suboptimal amount of at least one form of tapentadol, and at least one antagonist, wherein the said antagonist improves the efficacy of tapentadol and reduces the adverse side effects of tapentadol, and the said dosage form provides effective clinical relief for at least 12 hours when administered to a human patient.

The present invention provides a method of administering an oral dosage form comprising an optimal or suboptimal amount of at least one form of tapentadol, and at least one antagonist, wherein the said antagonist improves the efficacy of tapentadol and reduces the adverse side effects of tapentadol, and the said dosage form provides effective clinical relief for up to about 24 hours when administered to a human patient.

Another object of the present invention is to provide a dosage form comprising at least one form of tapentadol, and at least one opioid antagonist, wherein the dosage form, upon oral administration, results in an adverse event profile which is better than the adverse event profile resulting from the administration of a dosage form without an opioid antagonist.

Another object of the present invention is to provide a dosage form comprising at least one form of tapentadol, and at least one opioid antagonist, wherein the dosage form, upon oral administration, results in fewer occurrences of dizziness or vertigo than would result from the administration of a dosage form without an opioid antagonist.

In one embodiment, the present invention provides a dosage form comprising at least one form of tapentadol, and at least one opioid antagonist, wherein the dosage form, upon oral administration, results in fewer occurrences of nausea than would result from the administration of a dosage form without an opioid antagonist.

In one embodiment, the present invention provides a dosage form comprising at least one form of tapentadol, and at least one opioid antagonist, wherein the dosage form, upon oral administration, results in fewer occurrences of vomiting than would result from the administration of a dosage form without an opioid antagonist.

In one embodiment, the present invention provides a dosage form comprising at least one form of tapentadol, and at least one opioid antagonist, wherein the dosage form, upon oral administration, results in fewer occurrences of headache than would result from the administration of a dosage form without an opioid antagonist.

In one embodiment, the present invention provides a dosage form comprising at least one form of tapentadol and an opioid antagonist wherein the dosage form comprises from about 25 to about 800 mg of one form of tapentadol.

The dosage forms of the present invention includes, but is not limited to, a transdermal delivery system, an oral mucosal delivery system, a composition for intranasal administration, an injectable composition, and a solid oral composition.

The present invention is unique because tapentadol is present at such a level that the opioid antagonist has selective antagonist action at excitatory, but not inhibitory of opioid receptors. However, since dosage form of present invention has opioid antagonist performing dual role of improving the efficacy and reducing the adverse side effects of tapentadol, the opioid agonist becomes effective when administered at reduced doses which would otherwise be sub-analgesic. It may be possible to achieve an analgesic effect with 10-100 times lower doses of at least one bimodally acting tapentadol with the excitatory opioid receptor antagonists of the invention than when tapentadol is administered alone. This is because the excitatory opioid receptor antagonists may improve the efficacy by reducing the anti-analgesic excitatory side effects of tapentadol. Therefore, in certain preferred embodiments of the invention, tapentadol included in the dosage form is delivered in an amount which is less than that which has been typically administered for affecting analgesic effect. In certain embodiments of the invention, tapentadol is delivered such that the amount of tapentadol included in the dosage form is, e.g., about 10 to about 100 times less than the amount of tapentadol typically dosed over the dosing interval.

The opioid antagonists that can be used include, but not limited to, naloxone, naltrexone, diprenorphine, etorphine, dihydroetorphine, nalinefene, cyclazacine, levallorphan, pharmaceutically acceptable salts thereof and mixtures thereof. In certain referred embodiments, the opioid antagonist is naloxone or naltrexone.

In other embodiments, the antagonist is selected from the group consisting of naloxone, naltrexone, nalmefene, methylnaltrexone, nalide, nalmexone, nalorphine, nalbuphine, haloperidol, promethazine, fluphenazine, perphenazine, levomepromazine, thioridazine, perazine, chlorpromazine, chlorprothixine, zuclopentixol, flupentixol, prothipendyl, zotepine, benperidol, pipamperone, melperone and bromperidol.

In one preferred embodiment, the ratio of opioid agonist such as tapentadol to opioid antagonist is 1:3. That is opioid antagonist is present three times the amount of an opioid agonist. This ratio is arrived to accommodate that opioid antagonist performs dual roles of enhancing the analgesic potency of the opioid agonist such as tapentadol and attenuate the side effects and also prevent its abuse whenever the dosages form is tempered upon.

In other preferred embodiments, the slow release oral dosage form provides a formulation comprising a tapentadol and an opioid antagonist released over a period of time, such that when the dosage form is administered to a human, the blood levels of tapentadol is maintained throughout the dosing period at an therapeutically effective level, and the antagonist at a level sufficient to decrease the side effects associated with tapentadol but not sufficient to negate the analgesic effect of tapentadol. The ratio of tapentadol with the antagonist is about 1:1 to about 5000:1 by weight, more preferably from about 50:1 to 1000:1 and still more preferably from about 50:1 to about 500:1 In other preferred embodiments of the invention the amount of the opioid receptor antagonist administered is about 100 to about 10000 fold less than the amount of the opioid agonist administered.

The slow release oral dosage forms according the instant invention may be formulated using the standard methods available to one skilled in the art. For Example: The slow release tablets comprise tapentadol and antagonist in a slow release matrix. The slow release matrix of this invention may include hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting slow release of tapentadol may be deployed. The hydrophobic material in preferred embodiment include pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate)copolymer, polyacrylamide, aminoalkyl methacrylate copolymer, poly (methacrylic acid anhydride), and glycidyl methacrylate copolymers. To achieve the desired release profile, it may be necessary to use a combination of two co-polymers.

The instant invention use alkyl celluloses to achieve the desired release profile. In one embodiment, the formulation uses ethyl cellulose though the persons skilled in the art would easily substitute an alternate material and such substitutes are encompassed in the present invention. The commercially-available aqueous dispersions of ethylcellulose are Aquacoat.R® or Surelease.R® prepared according to standard techniques. These may be optionally mixed with a plasticizer prior their use in a coating. Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit.R® RL/RS lacquer solutions include polyethylene glycols, propylene glycol, diethyl phthalate, castor oil, and triacetin. A preferred plasticizer of this invention in aqueous dispersions is triethyl citrate.

The instant invention envisages the use of film coat, in combination with the others, to achieve a desired in-vitro release rate. The slow release coating formulations of the present invention may also include ingredients such as coating additives that are non-toxic, inert, and tack-free.

The dosage forms, of instant invention, comprising tapentadol and opioid antagonist may optionally be coated with one or more materials to control the release of opioid agonist protect the formulation. In an embodiment of this invention, the formulations are coatings are provided to enable either pH-dependent or pH-independent release, upon exposure to stomach fluids. The use of a pH-sensitive coating serves to release tapentadol in the targeted areas of the gastro-intestinal tract so that the absorption profile is is capable of providing at least from about eight hours to up to about twenty-four hours of clinical effect to a patient. However, when a pH-insensitive coating is used, the coating is prepared in way to facilitate an optimal release of the tapentadol regardless of pH-changes in the GI tract. It is also possible to formulate instant inventions such that a portion of the dose is released in one targeted area of the GI tract and the reminder of the dose is released in another targeted area of the GI tract such as the small intestine.

The formulations according to the present invention that utilize pH-sensitive coatings may be use among other things ingredients such as shellac, cellulose acetate phthalate (CAP), polyvinyl acetate phthalate (PVAP), hydroxypropylmethylcellulose phthalate, and methacrylic acid ester copolymers, zein, and the like. There are a family of copolymers synthesized from diethylaminoethyl methacrylate and other neutral methacrylic esters that are commercially available as Eudragit R® from Rohm Tech, Inc. There are several different types of Eudragit R® that swell at different pH and there others such as Eudragit R® RL and Eudragit RS® that are though water swellable, are pH-insensitive in a dosage form.

In certain preferred embodiments, the substrate in a tablet core bead or a matrix particle containing the tapentadol and opioid antagonist combination is coated with a hydrophobic material such as alkyl cellulose or an acrylic polymer or a combination thereof. The coating according to this invention may be an organic or an aqueous solution or dispersion and to extent from about 2 to about 25% of the substrate weight in order to achieve a desired sustained release profile.

The composition according to the invention may be presented, for example, as granules, spheroids, pellets, multiparticulates, capsules, patches tablets, sachets, controlled release suspensions, or in any other suitable dosage form incorporating such granules, spheroids, pellets or multiparticulates.

The one or more of active ingredient in the combination according to the present invention may suitably be incorporated in a matrix. This may be any matrix, known to a person skilled the art, that affords slow release tapentadol over at least a twelve hour period and preferably that affords in-vitro dissolution rates and in vivo absorption rates of tapentadol within the therapeutically effective ranges. The combination according to the present invention may preferably use a slow release matrix. Alternatively, normal release matrices having a coating which provides for slow release of the tapentadol may be used.

The slow release matrix employed in the combination of this invention may also contain other pharmaceutically acceptable ingredients which are conventional in the pharmaceutical art such as diluents, lubricants, binders, granulating aids, colorants, flavourants, surfactants, pH adjusters, anti-adherents and glidants, e.g. dibutyl sebacate, ammonium hydroxide, oleic acid and colloidal silica. Any known diluent e.g. microcrystalline cellulose, lactose and dicalcium phosphate may be used to prepare this combination. Suitable lubricants are e.g. magnesium stearate and sodium stearyl fumarate. Suitable binding agents are e.g. hydroxypropyl methyl cellulose, polyvidone and methyl cellulose. Suitable disintegrating agents are starch, sodium starch glycolate, crospovidone and croscarmellose sodium.

The surface actives that are suitable for this invention are Poloxamer 188.™, polysorbate 80 and sodium lauryl sulfate. The suitable flow aids for this invention are talc colloidal anhydrous silica. Similarly, the suitable water soluble polymers that may be used to prepare the matrix are polyethylene glycols with molecular weights in the range 1000 to 6000. The combination comprising the slow release tapentadol according to the invention may conveniently be film coated using any film coating material conventional in the pharmaceutical art but preferably an aqueous film coating is used.

The oral dosage form of the present invention may further include, in addition to tapentadol and antagonist, a second analgesic that may or may not be synergistic with tapentadol. The second analgesic is selected from the group consisting of NSAID, Acetaminophen, a GABA analogue, a Serotonin Norepinephrine reuptake inhibitor (SNRI), a Cyclo-oxygenase-(COX)-inhibiting nitric oxide donator, a HT Agonist and a Proton Pump Inhibitor., tramadol, hydromorphone, faxeladol, axomadol, oxycodone, hydrocodone, fentanyl, morphine, pharmaceutically acceptable salts thereof and mixtures thereof. They include any drug used to relieve pain including paracetamol (acetaminophen), ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well known to those skilled in the art. Other classes of drugs not normally considered analgesics are used to treat neuropathic pain syndromes; these include tricyclic antidepressants and anticonvulsants. Still further the additional drugs include antitussive, expectorant, decongestant, antihistamine drugs, local anesthetics, and the like types.

In certain preferred embodiments of the invention, the slow release oral dosage form comprises tapentadol and an opioid antagonist in combination with acetaminophen. It is possible that the slow release formulations prepared in accordance with the present invention include a wide range of dosages of acetaminophen, easily to known to a person skilled in art, such as dose than the 50-650 mg dose, but that dose will be released in a slow release manner over a longer dosing interval over 8 hours or more.

In certain embodiments, the dosage form according to the present invention comprises at least one form of tapentadol and at least one opioid antagonist, wherein the dosage exhibits a dissolution profile, when measured in a USP Type II paddle apparatus at 100 rpm at 37° C. in 900 ml simulated gastric fluid/simulated intestinal fluid (SGF/SIF) combination, such that about 8% of tapentadol is released after two hours, about 22% of tapentadol is released after 4 hours, about 48% of tapentadol is released after 8 hours, about 70% of tapentadol is released after 12 hours, about 78% of tapentadol is released after 16 hours, and not less than 80% of tapentadol is released after 20 hours.

The combinations as per this invention may comprise a normal release matrix having a slow release coating. Preferably the combination comprises film coated spheroids containing the active ingredient and a spheronising agent. The spheronising agent may be any suitable pharmaceutically acceptable material which may be spheronised together with the active ingredient to form spheroids. A preferred spheronising agent as per this invention is microcrystalline cellulose. The microcrystalline cellulose used may suitably be, for example, Avicel PH 101 or Avicel PH 102 (Trade Marks, FMC Corporation). The spheroids may optionally contain other pharmaceutically acceptable ingredients conventional in the pharmaceutical art such as binders, bulking agents and colorants. Suitable binders may include water soluble polymers, water soluble hydroxyalkyl celluloses such as hydroxypropylcellulose or water insoluble polymers (which may also contribute controlled release properties) such as acrylic polymers or copolymers for example ethylcellulose. Suitable bulking agents include lactose.

The spheroids are coated with a material which permits release of the active ingredient at a slow rate in an aqueous medium. Suitable slow release coating materials that may be used in this invention include water insoluble waxes and polymers such as polymethylacrylates (for example Eudragit polymers,) or water insoluble celluloses, particularly ethylcellulose. Optionally, water soluble polymers such as polyvinylpyrrolidone or water soluble celluloses such as hydroxypropylmethylcellulose or hydroxypropylcellulose may be included. Optionally other water soluble agents such as polysorbate 80 may be added.

Further in an alternative embodiment, a flux-enhancing agent can also be included in the membrane or slow release coating can include one of the above-described polymers. The flux enhancing agent can increase the volume of fluid imbibed into the core to enable the dosage form to dispense substantially all of the tapentadol through the passage and/or the porous membrane. The flux-enhancing agent can be a water-soluble material or an enteric material. Examples of the preferred materials that are useful as flux enhancers include but not limited to sodium chloride, potassium chloride, sucrose, sorbitol, mannitol, polyethylene glycols (PEG), propylene glycol, hydroxypropyl cellulose, hydroxypropyl methycellulose, hydroxypropyl methycellulose phthalate, cellulose acetate phthalate, polyvinyl alcohols, methacrylic acid copolymers, poloxamers (such as LUTROL F68, LUTROL F127, LUTROL F108 which are commercially available from BASF) and mixtures thereof. A preferred flux-enhancer used in this invention is PEG 400.

The flux enhancer may also be a water miscible/soluble drug such as Tapentadol or its pharmaceutically acceptable salts, or the flux enhancer may be a drug that is soluble under intestinal conditions. If the flux enhancer is a drug, the present pharmaceutical composition has an added advantage of providing an immediate release of the drug that has been selected as the flux enhancer. The flux enhancing agent dissolves or leaches from the membrane or sustained release coating to form channels in the membrane or sustained release coating which enables fluid to enter the core and dissolve the active ingredient. In the preferred embodiment, the flux enhancing agent comprises approximately 0 to about 40% of the total weight of the coating, most preferably about 2% to about 20% of the total weight of the coating.

A commonly known excipient such as a plasticizer may also be used for preparing the membrane or slow release coating Some commonly known plasticizers include but not limited to adipate, azelate, enzoate, citrate, stearate, isoebucate, sebacate, triethyl citrate, tri-n-butyl citrate, acetyl tri-n-butyl citrate, citric acid esters, and all those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate and the like. Though the exact amount used depends on the type of plasticizer used, typically amounts from about 0 to about 25% are used, and preferably about 2% to about 15% of the plasticizer can be used based upon the total weight of the membrane or sustained release coating.

Generally, the membrane or slow release coating around the core will comprise from about 1% to about 20% and preferably about 2% to about 10% based upon the total weight of the core and coating.

The membrane or sustained release coating surrounding the core can further comprise a passage that will allow for controlled release of the drug from the core in a preferred embodiment. As used herein the term passage includes an aperture, orifice, bore, hole, weakened area or a credible element such as a gelatin plug that erodes to form an osmotic passage for the release of the tapentadol from the dosage form. Passages used in accordance with the subject invention are well known and are described in U.S. Pat. Nos. 3,845,770; 3,916,899; 4,034,758; 4,077,407; 4,783,337 and 5,071,607.

The following examples are shown for illustrating the invention related to 1) a dosage form comprising an optimal or suboptimal amount of at least one form of tapentadol and at least one opioid antagonist, 2) a slow release dosage form comprising optimal or suboptimal amount of at least one form of tapentadol and at least one opioid antagonist, and 3) a pharmaceutical composition comprising optimal or suboptimal amount of at least one form of tapentadol and at least one opioid antagonist, and at least one additional analgesic drug. All formulations are intended to enhance analgesic potency and/or reduce one or more adverse effects The examples further illustrate a method of treating pain and pain related conditions by administering to a patient in need thereof, optimal or suboptimal amount of at least one form of tapentadol and at least one opioid antagonist to enhance analgesic potency and/or attenuate one or more adverse effects of tapentadol and a method of treating pain and pain related conditions by administering to a patient in need thereof, a slow release tapentadol and a second analgesic. The person skilled in the art will know how the dosage forms and methods of administrations may be modified using other techniques known in the art.

EXAMPLE 1

TABLE 1

| Slow Release Tapentadol 50 mg | |
|---|---|
| Tapentadol HCl | 50 |
| Eudragit RSPO | 88 |
| Ethylcellulose | 4.5 |
| Stearyl Alcohol | 35 |
| Total | 177.5 |
| Naltrexone Pellets | |
| Naltrexone HCl | 1 |
| Eudragit RSPO + Eudragit RLPO (6:1) | 80 |
| Stearic Acid | 50 |
| Total | 131 |
| Slow Release Tapentadol and Slow Release Naltrexone Dosage | |
| Tapentadol Pellets | 177.5 |
| Naltrexone Pellets | 131 |
| Total | 308.5 |

Manufacturing Process:

Tapentadol Hydrochloride, Eudragit and ETHOCEL are blended together in a blender. To the well blended mix, milled stearyl alcohol is added and the contents were thoroughly mixed together and fed an extruder and later a pelletizer. The pellets are screened and sieved to obtain the required tapentadol pellets. In parallel, Naltrexone pellets were prepared following a similar procedure. The final capsules comprising tapentadol and Naltrexone were prepared by filling the required quantity of tapentadol pellets and naltrexone pellets.

EXAMPLE 2

TABLE 2

| Slow Release Tapentadol 100 mg | Quantity mg |
|---|---|
| Core | |
| Tapentadol HCl | 100.0 |
| Polyvinyl Alcohol | 2.0 |
| Colloidal Silicon Dioxide (Abrosil ® 200) | 1.0 |
| Sodium Stearyl Fumerate | 1.0 |
| Water* | Q.S |
| Core Weight | 104.0 |
| Coat | |
| Ethylcellulose (Ethocel ® PR 100) | 9.20 |
| Polyvinylpyrrolidone (Kollidon ® 90F) | 4.14 |
| Dibutyl Sebacate | 2.66 |
| Denatured Alcohol* | Q.S |

*Removed during the process

Manufacturing Process;

Core Preparation; Tapentadol HCl and colloidal silicon dioxide were mixed and passed through a 1.0 mm screen. Polyvinyl alcohol was dissolved in purified water. The mixed tapentadol HCl and colloidal silicon dioxide powder was granulated with the aqueous solution of polyvinyl alcohol in a fluidized bed granulator, Glatt GPCG1 and then dried. After granulation, the granules were blended with sodium stearyl fumarate and then passed through a 1.0 mm screen. The blend was then compressed into tablet cores using a Manesty Betapress.

Coating Preparation; The ethyl alcohol and isopropanol in appropriate quantity were weighed and mixed together. Dibutyl sebacate and ethylcellulose were added to and dissolved in the ethyl alcohol and isopropyl alcohol midst of constant stirring with a propeller stirrer, Coframo RZR1 and polyvinylpyrrolidone was added. The solution was stirred until all components were dissolved. The solution was passed through a high pressure homogenizer.

The tablet cores were coated using the coating solution in a perforated coating pan, O'Hara Labcoat I11 36" Pan, Vector LCDS. The coating parameters are listed in Table 3;

TABLE 3

| Coating Parameters | |
|---|---|
| Inlet Temperature: | 48.5-49.5' C. |
| Outlet Temperature: | 38.5-39.5' C. |
| Bed Temperature: | 37.5-38.5' C. |
| Spray Rate: | 300 g/minute |
| Atomizing Air/Pattern: | 25/25 psi |
| Distance gun/Bed: | 6" |
| Distance between guns: | 6" |
| Pan speed: | 12 rpm |
| Coating Amount Diameter: | |
| Thickness: | 6 mm |
| Cup Height: | 4.65 mm |
| Surface: | 1.02 mm |
| Percentage: | 112 mm² |
| Amount: | 16 mg |

Dissolution Studies

The tablets comprising slow release tapentadol and at least one pharmaceutical excipient, formulated according Examples 1 was evaluated for dissolution profiles with an apparatus USP basket of 10 mesh as per following conditions in Table 4;

TABLE 4

| Dissolution Study Conditions | |
|---|---|
| Apparatus: | USP basket of 10 Mesh |
| Medium of dissolution | 0.1N Hydrochloride |
| Vessel Volume | 900 ml |
| Temperature | 37'-38" C. |
| Wavelength | 271 nm |
| Flow Cell Measurement | 1 CM |
| Speed | 75 RPM |
| Run time | 900 minutes |
| Interval for sampling | 30 Minutes |

The composition of instant invention exhibits an in vitro dissolution profile (measured using the USP Basket Method at 75 rpm in 900 ml 0.1 N HCl at 37.degree. C.) such that after 2 hours, from about 0% up to about 30% (by weight) of tapentadol is released, after 4 hours, from about 5% to about 55% (by weight) of tapentadol is released, after 12 hours, more than about 50% (by weight) of tapentadol is released, and after 24 hours, more than about 80% (by weight) of tapentadol is released.

Still further, the composition of instant invention exhibits an in vitro dissolution profile (measured using the USP Basket Method at 75 rpm in 900 ml 0.1 N HCl at 37' C.) such that after 2 hours, from about 0% up to about 30% (by weight) of tapentadol is released, after 4 hours, from about 5% to about 22% (by weight) of tapentadol is released, after 6 hours, from about 15% to about 38% (by weight) of the tapentadol is released, after 8 hours, more than about 40% (by weight) of tapentadol is released.

Further, the composition of instant invention exhibits an in vitro dissolution profile (measured using the USP Basket Method at 75 rpm in 900 ml 0.1 N HCl at 37' C.) such that after 2 hours, from about 2% to about 10% of tapentadol is released, after 4 hours, from about 12% to about 20% of tapentadol is released, after 6 hours, from about 30% to about 38% of tapentadol is released, after 8 hours, from about 48% to about 56% of tapentadol is released, after 10 hours, from about 64% to about 72% of tapentadol is released, and after 12 hours, more than about 76% of tapentadol is released.

EXAMPLE 3

Pregabalin Combination

TABLE 5

| Pregabalin Combination | |
|---|---|
| First Active Ingredient mg/tablet | |
| Tapentadol Hydrochloride | 100 |
| Lactose | 65 |
| Ethyl Cellulose | 16 |
| Cetostearyl Alcohol | 43 |
| Magnesium Stearate | 2 |
| Talc | 4 |
| Hydroxyethyl Cellulose | |
| Water | qs |
| Coat | |
| Hydropropylmethylcellulose | 0.75 |
| Hydroxymethylcellulose | 3.75 |
| Opaspray | 2.6 |
| PEG 400 | 0.6 |
| Talc | 0.3 |
| Water | q.s |
| Second Active Ingredient | |
| Pregabalin | 250 |
| Povidone K 30 USP | 1 |
| Lactose | 25 |
| Sodium starch Glycolate | 7.5 |
| Poloxamer 188 | 3 |
| HPMC | 1.5 |
| PEG 8000 | 0.4 |
| Titanium Dioxide | 0.4 |
| Wax | 0.2 |

EXAMPLE 4

Naparoxen Combination

TABLE 6

| Naproxen Combination | |
|---|---|
| First Active Ingredient mg/tablet | |
| Tapentadol Hydrochloride | 100 |
| Lactose | 65 |

TABLE 6-continued

Naproxen Combination

| Ethyl Cellulose | 16 |
| Cetostearyl Alcohol | 43 |
| Magnesium Stearate | 2 |
| Talc | 4 |
| Hydroxyethyl Cellulose | |
| Water | qs |
| Coat | |
| Hydropropylmethylcellulose | 0.75 |
| Hydroxymethylcellulose | 3.75 |
| Opaspray | 2.6 |
| PEG 400 | 0.6 |
| Talc | 0.3 |
| Water | qs |
| Second Active Ingredient | |
| Naproxen | 250 |
| Povidone K 30 USP | 1 |
| Lactose | 25 |
| Sodium starch Glycolate | 7.5 |
| Poloxamer 188 | 3 |
| HPMC | 1.5 |
| PEG 8000 | 0.4 |
| Titanium Dioxide | 0.4 |
| Wax | 0.2 |

Manufacturing Process, 1: Slow Release Tapentadol Hydrochloride and Naproxen

The combination comprising a slow release tapentadol hydrochloride and naproxen were manufactured in two phases using standard grannulation and coating processes. In phase I, the Tapentadol Hydrochloride was formulated into a core which was further coated with slow release coat to get a slow release tapentadol core. In Phase II, the above prepared coated slow release Tapentadol hydrochloride core was coated with an immediate release layer comprising Naproxen. The details are given below;

Phase I; Core preparation: Tapentadol HCl is mixed with microcrystalline cellulose and colloidal silicone dioxide and one or mixture of filler and granulated using suitable method known in the art using a binder solution comprising Polyvinylpyrrolidone or polyvinyl alcohol. The granulated tapentadol hydrochloride was dried and screened. This is further lubricated using hydrogenated vegetable oil with or without glidant. The lubricated blend is compressed into tablets using a compression machine.

Coating Solution and Coating: The coating solution is prepared using aqueous dispersion of water insoluble water permeable polymer of Ethylcellulose with water soluble polymer of Polyvinylpyrrolidone or hydroxy propyl methyl cellulose. Polyethylene glycol mixture prepared using propeller stirrer and the same is homogenized using suitable homogenizer. The core tablets are coated using coating solution using standard coater like O'Hara pan coater tip set at 4" at a spray rate of 25 mL/gun/min, exhaust temperature of around 45'C, an atomization pressure from 10-35 psi at a pan speed of 5-8 rpm, using airflow 350 CFM.

Phase II: In phase II, Naproxen formulation prepared using granulation technique known in the art and then blended with disintegrant and lubricant.

Final Formulation: Tapentadol slow release tablets prepared in Phase I is coated with lubricated blend of Naproxen formulation using compression coating machine where Tapentadol slow release tablets is used as a core and an immediate layer of Naproxen formulation forms an outer layer.

The naproxen coating was applied to coated 100 mg tapentadol hydrochloride tablets using the above mentioned coater. Over this naproxen coated seal coated 100 mg tapentadol hydrochloride tablets, color coating was done using similar coat. The spraying was done at a temperature of 46-47' C, atomization pressure of 40-60 psi at a spray rate of 180 grams per minute/three guns. The pan speed was at 4-8 rpm and air volume of 1000±100.

Finally, optionally color coated tablets were dried and polished using Cindrella wax and the finished final tablets were packaged in a HDPE bottle with a suitable desiccant and subjected appropriate stability and clinical studies. In vitro dissolution studies were conducted herein for determining the in vitro dissolution profile of Tapentadol Hydrochloride in the combination as per conditions listed in Table 6. In Example 1, we used a combination comprising 100 mg of slow release tapentadol and 250 mg naproxen.

EXAMPLE 5

In yet another example, the invention discloses a pharmaceutical composition which can effectively be used in the treatment of pain and pain related diseases wherein the compositions comprise a therapeutically effective amount of a slow release tapentadol and naltrexone hydrochloride to a patient in need can be formulated in other ways. For Example, the combination comprising a slow release tapentadol and an opioid antagonist such as naltrexone hydrochloride was prepared as a bilayer tablet as exemplified below:

Layer 1:

| Tapentadol HCl | 100 mg |
| Microcrystalline cellulose | 10-25% |
| Polyvinyl alcohol | 3-5% |
| Ethylcellulose (5-20 cp) | 10-20% |
| Hydroxyethyl cellulose | 5-15% |
| Colloidal silicon dioxide | 2-5% |
| Sodium stearyl fumarate | 1-2% |

Layer 2:

| Naltrexone Hydrochloride | 1 mg |
| Microcrystalline cellulose | 5-20% |
| Povidone | 10-15% |
| Crosscarmellose sodium | 5-10% |
| Magnesium stearate | 0.5-2% |

Preparation of Layer 1: Tapentadol Hydrochloride, microcrystalline cellulose and colloidal silicon dioxide were granulated with polyvinyl alcohol and dried. The dried granules are mixed with Ethylcellulose and Hydroxyethylcellulose and lubricated with Sodium stearyl fumarate.

Preparation of Layer 2: Naltrexone Hydrochloride mixed with microcrystalline cellulose was granulated with povidone. Granules are dried and mixed with Crosscarmellose sodium and finally lubricated with Magnesium stearate.

Compression: Layer 1 and Layer 2 are loaded into the hopper of bilayer rotary compression machine and compressed with a desired hardness.

EXAMPLE 6

A dosage form comprising tapentadol and naltrexone hydrochloride was prepared to according the formal in Table 7.

TABLE 7

TABLE 6

| Morphine Micellar Formulation Ingredient | Quantity grams |
|---|---|
| Tapentadol | 50 |
| Naltrexone Hydrochloride | 1 |
| Polyoxyethylene-9-Lauryl Ether | 9 |
| Glycerin | 12 |
| Phenol | 10 |
| Sodium Lauryl Sulfate | 8 |
| Sodium Glycocholate | 6 |
| Absolute Alcohol | 40 |
| Water* | 200 |
| Total Weight | 136 |

*Removed during the process

Manufacturing Process: Tapentadol hydrochloride, naltrexone hydrochloride, polyoxyethylene-9-lauryl ether, glycerin, phenol, sodium lauryl sulfate, sodium glycocholate were all mixed in absolute alcohol with through shaking on automatic shaker and diluted with water to prepare 200 ml micellar solution.

EXAMPLE 7

TABLE 8

| Tapentadol-Naltrexone Layer | |
|---|---|
| Tapentadol Hydrochloride | 50 |
| Naltrexone Hydrochloride | 1 |
| Povidone | 6 |
| Triacetin | 2 |
| Eudragit RS30D | 12 |
| Lactose | 60 |
| Talc | 3 |
| Magnesium Stearate | 1.5 |
| Stearyl Alcohol | 15 |
| Water | 60 |
| Seal Coat | |
| Opadry White Y-5-7068 | 2.5 |
| Water | 15 |
| Final Tablet Weight | 167.5 |

Manufacturing Process; Eudragit and triacetin were mixed together to prepared a solution into which naltrexone hydrochloride was dissolved. The solution was applied over a mixture of oxycodone HCL, lactose and Povidone in a fluid bed granulator, milled in a mill, and stearyl alcohol melt was applied to this granulation. The granulation was cooled and mixed with magnesium stearate and talc and compressed. The compressed tablets comprising tapentadol HCl and naltrexone hydrochloride were coated with a seal coat optionally.

EXAMPLE 8

TABLE 9

| Tapentadol Beads | |
|---|---|
| | Unit Quantity mg |
| Tapentadol Beads | |
| Tapentadol HCl | 50 |
| Polyvinylpyrrolidone | 4 |
| Inert Beads | 20 |
| Eudragit RS30 | 2 |
| Lactose | 15 |
| Opadry II (Colorcon) | 5 |
| Water | 35 |
| Slow Release Coat | |
| Eudragit RS30+ Eudragit RL30D (9.5:1) | 5.12 |
| Ethyl Citrate (Aldrich W308307) | 1.01 |
| Talc | 1.77 |
| Opadry II (Colorcon) | 5.5 |
| Water | 8 |
| Tapentadol Bead Weight | 125.4 |
| Naltrexone Beads | |
| Naltrexone HCl | 1 |
| Sugar Spheres NF (Paulaur (Cranbury, NJ) | 75 |
| Talc | 10 |
| Polyvinylpyrrolidone (Plasdone 28-32) | 0.95 |
| Water | 25 |
| Opadry II (Colorcon) | 5 |
| Slow Release Coat | |
| Eudragit RS30D | 14.1 |
| Polysorbate 20 | 0.05 |
| Acetyl Tributyl Citrate (ATBC) | 3.38 |
| Talc | 12.5 |
| Opadry II (Colorcon) | 5 |
| Water | 45 |
| Naltrexone Beads Weight | |
| Tapentadol HCl Beads | 125.4 |
| Naltrexone HCl Beads | 127.98 |
| Total Weight | 252.38 |

*Removed while processing

Manufacturing Process: Tapentadol HCl beads and Enhancing naltrexone HCl beads were prepared according to the formula in Table 1. Specifically tapentadol and polyvinypyrrolidine were dissolved in water and mixed with others before applying to sugar beads at 60' C using standard procedures. The tapentadol beads were coated with a coating solution comprising Eudragit, Ethyl Citrate, and talc dispersion. Naltrexone beads were prepared by mixing all constituents in a mixer. The fine mixture was granulated with water, extruded in an extruder at desired size and classified by a screener. The screened naltrexone hydrochloride beads were coated with a coating solution prepared by dissolving Eudragit RS30D, Polysorbate 20, Acetyl Tributyl Citrate (ATBC) and dispersing talc. The beads were dried and incorporated into capsules along with tapentadol HCl beads and enhancing naltrexone beads to prepare dosage form that comprises tapentadol and an amount of an opioid antagonist effective to enhance the analgesic potency of tapentadol and an amount of naltrexone hydrochloride effective to reduce the abuse of tapentadol. The enhancing beads and the anti abuse beads of naltrexone hydrochloride can be optionally color coated to make look indistinguishable from another.

EXAMPLE 9

Method of Administration

The objects of the present inventions were established using five well controlled human clinical trials. The trials established 1) a method for treating pain in a subject by co-administering to the human subject at least form of tapentadol and at least one opioid antagonist, 2) a method for treating pain in a human subject by administering to the human subject a fixed dose combination comprising at least one form of slow release tapentadol and at least one opioid antagonist and, 3) a method for treating pain in a human subject by administering to the human subject a fixed dosage form comprising of slow release tapentadol and at least one additional drug such as naproxen or pregabalin and an opioid antagonist, 4) a method of administering a combination comprising tapentadol and naltrexone at three different dosage concentrations to identify an optimum concentration of naltrexone. All studies were conducted to evaluate the effectiveness of the combinations to enhance the analgesic potency of tapentadol and further attenuate the adverse side effects.

Study 1; Treatment of Humans with Tapentadol in Combination with Naltrexone, Naloxone and Nalmefene;

In order to establish the invention, Nectid conducted a human clinical study involving over 250 pain patients. The patients were administered with tapentadol alone or in combination with three different opioid antagonists; naltrexone, naloxone and nalmefene. The analgesic efficacy of the co-administered combination of tapentadol and an opioid antagonist, in comparison with positive and negative controls, was measured. The effects of such combination on the side effects such as dizziness, nausea, sedation, etc were also measured.

In this randomized, double-blind, active-controlled and placebo-controlled, parallel-group study, study, one objective was to determine whether an opioid antagonist such as naloxone (hereafter referred to as N1), naltrexone hydrochloride (hereafter referred to as N2), and nalmefene (hereafter referred to as N3) enhance the analgesic properties of tapentadol hydrochloride (hereafter referred to as Tap) in human subjects/patients with pain following dental surgery. Another objective was to evaluate whether an opioid antagonist such as naltrexone reduced tapentadol induced adverse side effects in humans.

Three hundred four (304) subjects were actually entered in the study and among them 254 completed the study. A positive control Tapentadol and a negative control (placebo) were used and the human subjects were randomized into one of the following five treatment groups: The numbers of subjects were actually assigned to the five treatment groups are as follows:

| GROUP | DRUGS | No. of Subjects (N) |
| --- | --- | --- |
| Group 1 | Placebo with Placebo | 51 |
| Group 2 | Tap (50 mg) with Placebo | 50 |
| Group 3 | Tap (50 mg) with Naloxone (0.1 mg) | 51 |
| Group 4 | Tap (50 mg) with Naltrexone (0.1 mg) | 52 |
| Group 5 | Tap (50 mg) with Nalmefene (0.1 mg) | 50 |

A positive control (Tap, Group 2) was used to determine the sensitivity of the clinical end points. A negative control (placebo, Group 1) was used to establish the frequency and magnitude of changes in clinical end points that may occur in the absence of an active treatment. A single oral dose of study medication was administered when the subject experienced moderate to severe pain following the surgical extraction of three or four third-molars.

Study 2; Treatment of Humans with Slow Release Tapentadol in Combination with Naltrexone, Naloxone and Nalmefene;

In this randomized, double-blind, active-controlled and placebo-controlled, parallel-group study, study, one objective was to determine whether an opioid antagonist such as naloxone (hereafter referred to as N1), naltrexone hydrochloride (hereafter referred to as N2), and nalmefene (hereafter referred to as N3) improve enhances the analgesic properties of controlled release tapentadol hydrochloride in human subjects/patients. The effects of the combination of slow release tapentadol (hereafter referred to as slow release tapentadol or SRT) and an opioid antagonist on the analgesic potency were measured. The effects of such combination on the side effects such as dizziness, nausea, vomiting, etc were also measured. The slow release fixed dosage form was prepared according to the Example 4 and a slow release tapentadol prepared according to Example 2, co-administered in combination with naltrexone, naloxone and nalmefene, were used in the study.

Three hundred sixty six (366) subjects were actually entered in the study and among them 307 completed the study. A positive control (ST) and a negative control (placebo) were used and the human subjects were randomized into one of the following six treatment groups: The numbers of subjects were actually assigned to the six treatment groups are as follows:

| GROUP | DRUGS | No. of Subjects (N) |
| --- | --- | --- |
| Group 1 | Placebo with Placebo | 51 |
| Group 2 | SRT (100 mg) with Placebo | 49 |
| Group 3 | SRT (100 mg) with Naloxone (N1) (0.1 mg) | 53 |
| Group 4 | SRT (100 mg) with Naltrexone (N2) (0.1 mg) | 50 |
| Group 5 | SRT (100 mg) with Nalmefene (N3) (0.1 mg): | 52 |
| Group 6 | Example 7 (SRT 50 mg) with Naltrexone (N2) (1 mg) × 2: | 52 |

A positive control (SRT, Group 2) was used to determine the sensitivity of the clinical end points. A negative control (placebo, Group 1) was used to establish the frequency and magnitude of changes in clinical end points that may occur in the absence of an active treatment. A single oral dose of study medication was administered when the subject experienced moderate to severe pain following the surgical extraction of three or four third molars.

Study 3; Treatment of Humans with Tapentadol+Naproxen in Combination with Naltrexone;

Identical clinical trial methods were used to establish a method for treating pain in a subject by administering to the human subject a fixed dose combination comprising slow release tapentadol, and naproxen (Example 4) and an amount of naltrexone (N2) effective to enhance the analgesic potency of tapentadol, and attenuate an adverse side effect of tapentadol in a human 158 patients completed the study among the 182 who initially entered the trial. The five treatment arms used for this trial are listed below;

Group 1 (Placebo+Placebo); N=31
Group 2 FDC-Example 4 (SRT 50 mg+N 250 mg)+Placebo), N=30
Group 3 FDC-Example 4 (SRT 50 mg+N 250 mg)+Naltrexone (N2) (0.01 mg), N=32
Group 4 FDC-Example 4 (SRT 50 mg+N 250 mg)+Naltrexone (N2) (0.1 mg), N=33
Group 5 FDC-Example 4 (SRT 50 mg+N 250 mg Example 4)+Naltrexone (N2) (1 mg), N=32

A positive control FDC (SRT+Naproxen 250 mg, Group 2) was used to determine the sensitivity of the clinical end points. A negative control (Placebo, Placebo Group 1) was used to establish the frequency and magnitude of changes in clinical end points that may occur in the absence of an active treatment. A single oral dose of study medication was administered when the subject experienced moderate to severe pain following the surgical extraction of three or four third molars.

Inclusion Criteria: (1) male or female subjects of any race and at least sixteen years of age (a subject under eighteen years old participated only if emancipated or if a parent (or guardian) gave written informed consent); (2) able to speak and understand English and provide meaningful written informed consent; (3) outpatients in generally good health (in particular, the subject must have had no history of liver or kidney disease); (4) three or four third molars to be extracted (at least one tooth must be mandibular bony impacted) and the subject was considered to have had surgery significant enough to warrant an opioid analgesic; (5) an initial categorical pain intensity score of at least moderate on a scale of none, mild, moderate or severe, and the subject willing and able to complete the subject evaluations; (6) able to remain at the study site for at least eight hours following the dose of study drug; and (7) if female, postmenopausal, or physically incapable of childbearing, or practicing an acceptable method of birth control (IUD or hormones or diaphragm and spermicide or abstinence), and if practicing an acceptable method of birth control, must also have maintained a normal menstrual pattern for the three months prior to study entry and have had a negative urine pregnancy test performed within seven days before surgery.

Exclusion Criteria: (1) pregnant or breast-feeding; (2) have a history of hepatic or renal disease; (3) have a history of seizures, however, subjects with a history of juvenile febrile seizures could be included if there was no seizure history within the past ten years; (4) have a medical or psychiatric condition that compromises the subject's ability to give informed consent or appropriately complete the study evaluations; (5) have a known allergy or significant reaction to opioids, tapentadol, tramadol or naltrexone or naloxone or nalmefene; (6) have a history of chronic opioid use or opioid abuse within six months prior to study; (7) have used an anticonvulsant drug or tricyclic antidepressant drugs (including serotonin reuptake inhibitors and doses of St. John's Wort exceeding 1,000 mg per day) within four weeks prior to study entry; (8) currently taking a monoamine oxidase inhibitor (MAOI) or have taken a MAOI within two weeks prior to study entry; (9) consumed alcohol twelve hours prior to surgery and consumed alcohol or caffeine-containing products during the eight-hour observation period; (10) have taken any of the following drugs from at least four hours prior to dosing until the end of the study: analgesics, including aspirin, acetaminophen, nonsteroidal anti-inflammatory drugs (NSAIDS) and opioids (or opioid combinations); minor tranquilizers; muscle relaxants and antihistamines, as well as long-acting analgesics (e.g., long-acting NSAIDs) from twelve hours prior to dosing until completion of study observations; (11) have previously participated in this study; and (12) have been a participant in a study of an investigational drug or device within thirty days prior to this study.

Randomization: Randomization was used to avoid bias in the assignment of subjects to treatment, to increase the likelihood that known and unknown subject attributes (e.g., demographics and baseline characteristics) were evenly balanced across treatment groups, and to enhance the validity of statistical comparisons across treatment groups. Blinded treatment was used to reduce potential bias during data collection and evaluation of clinical end points. Prior to randomization, the following was accomplished: (1) informed consent; (2) medical history and demographics; (3) inclusion and exclusion criteria; and (4) prior and concomitant medication.

Subjects were assigned to treatment groups based on a computer generated randomization schedule prepared prior to the study. The randomization was balanced by using permuted blocks. Study drug for each subject was packaged and labeled according to this randomization code. In order to achieve balance among treatment groups with respect to starting pain, subjects with moderate starting pain were assigned medication with the lowest available number (next sequential treatment number in ascending order). Subjects with severe starting pain were assigned medication with the highest available number.

Medication: Following compliance with all Inclusion/Exclusion Criteria, all subjects with moderate to severe pain received one dose of study medication. Subjects received two capsules to take by mouth, one tapentadol, or placebo, the other naltrexone or placebo. Study medication was packaged per subject in study drug containers. Study medication was packaged in single-dose bottles identified by subject number and each contained 2 capsules. The label identified the study as PROTOCOL TA. Each bottle had a two-way drug disclosure label attached that listed the following information: subject number; cautionary statement; and general instructions. The labels bore the instructions: "Take contents when pain is moderate or severe." The tear-off portion of the label was removed prior to dispensing the study drug and attached unopened to the Label Page Case Report Form.

Any medications which a subject had taken in the twenty-four hours prior to surgery (including vitamins, thyroid or other prophylactic medication) had to be reported at the baseline visit on the concomitant medications Case Report Form. If the administration of any concomitant therapy became necessary due to treatment-emergent adverse events, it had to be reported on the appropriate Case Report Form. The medical monitor was notified in advance of (or as soon as possible after) any instances in which prohibited therapies according to the Exclusion Criteria were administered.

Pain Assessment Method: A pain assessment was performed pre-treatment. Following the dental surgery and, the subject's pain level was assessed by a trained observer. The subject reported the initial pain intensity by both (1) verbalizing one pain category (0=none, 1=mild, 2=moderate or 3=severe), and (2) using a Visual Analog Scale (VAS) of 0-100 mm where 0=no pain and 100=worst pain imaginable, by placing a single slash on the scale. The decision to medicate was based only on the categorical response. When the categorical pain level was moderate or severe, the subject then took the dose of study medication.

A pain assessment was also performed post-treatment. Following dosing, pain intensity and pain relief was recorded at the following times: 30 minutes, 60 minutes and hourly thereafter up to Hour 12 after dosing. All efficacy assessments were recorded by the subject in a diary in response to questioning by the trained observer. The observer questioned the subject for all observations and provided instruction as needed. Pain intensity was measured in response to the question, "How much pain do you have now?" with (1) subject response choices of none, mild, moderate and severe on a categorical scale, and (2) a mark on a 100-mm VAS. The pain relief relative to baseline was assessed in response to the question, "How much pain relief do you have now compared to when you took the medicine?" with subject response choices of none, a little, some, a lot, and complete. For the pain relief assessment, the subject was given a stopwatch and asked to stop it when any meaningful pain relief was felt.

Adverse events were assessed by non-directed questioning and recorded for the eight hours following dosing. A symptom checklist was also used for the most common adverse side effects of tapentadol in humans (e.g., dizziness, drowsiness, nausea, vomiting, headache, pruritus). These assessments were self-recorded by the subject in a diary at 30 minutes, 60 minutes and hourly thereafter up to Hour 8 after dosing At the end of eight hours, or at the termination of hourly observations if sooner than eight hours, a global assessment was made by the subject and the observer in response to the question, "How do you rate the pain relief?" with response choices of excellent, very good, good, fair or poor. Assessment of adverse events continued for at least one hour following rescue medication. Subjects not completing at least the Hour 1 observation period were considered not evaluable for efficacy and were replaced.

The study was completed after twelve hours of evaluation or upon receipt of rescue medication. Subjects could discontinue the study at any time.

Subjects who did not get adequate pain relief were provided a final set of pain observations. The subject was then given a rescue medication and discontinued from study. The subject was encouraged to wait at least until Hour 2 after administration of the study medication before using rescue medication. Subjects remedicating earlier than Hour 1 were not included in the analysis for efficacy. Subjects not remedicating during the eight hours of evaluation received a diary card and asked to record the time of remedication after they left the clinic.

Subjects were required to remain on the unit at least one hour after receiving rescue medication for adverse event evaluation. However, it was strongly recommended that these subjects remain at the site for the full eight hours after receiving study drug.

Efficacy Evaluations were performed using primary and secondary efficacy parameters. The primary efficacy parameters included: (1) 4-hour Total Pain Relief Scores (TOTPAR) (described below); (2) 4-hour Sum of Pain Intensity Differences (SPID), (categorical and VAS) (described below); (3) time to onset of meaningful pain relief within 8 hours; and (4) percent of subjects remedicating within 8 hours. The secondary efficacy parameters included: (1) 6 and 8 hour Total Pain Relief Scores (TOTPAR); (2) 6 and 8 hour Sum of Pain Intensity Difference (SPID), (Categorical and VAS); (3) hourly pain relief scores; (4) hourly pain intensity difference scores (categorical and VAS); (5) remedication time within 8 hours; and (6) global evaluations.

Safety Evaluations included: (1) Adverse Events (AE); and (2) symptom checklist. All adverse events occurring during the study had to be recorded on the case report forms. An adverse event was defined as any untoward medical occurrence connected with the subject being treated during the study, whether or not it was considered related to the study. All serious or unexpected adverse events, whether or not they were considered related to the study medication, had to be reported by telephone to the medical monitor immediately (no later than twenty-four hours after the investigator's receipt of the information) according to Ethical and Regulatory Requirements. The symptom checklist was used, as described above, to record the most common adverse side effects of tapentadol in humans.

In this study, standard measurements and determinations were utilized. For example, pain intensity was evaluated using both a categorical scale and a VAS, which are standard measurement instruments in analgesic studies. A global assessment of pain relief using a categorical scale and measurements of time to rescue medication are both standard measurements. The safety measures (history, adverse events, and concomitant medications) were also standard determinations.

Data Analysis: For the data analysis, computed parameters were as follows. The extent to which pain intensity changed over the test period was measured by the Total Pain Relief Score (TOTPAR) and the Sum of Pain Intensity Differences (SPID). TOTPAR was defined as the sum of Pain Relief Scores (PAR) (0=none, 1=a little, 2=some, 3=a lot, 4=complete) over the 4, 6 and 8-hour observation period. The Pain Intensity Difference (PID) at each time point was calculated as the difference between the Pain Intensity Score at Hour 0 and that score at the observation point (0=none, 1=mild, 2=moderate, 3=severe). SPID was defined as the sum of PIDs over the 4, 6 and 8-hour observation period. VAS-PID and VAS-SPID were defined similarly for the VAS scores. Missing values and evaluations performed after rescue medication were imputed by the Last Observation Carried Forward procedure (LOCF).

The primary analysis population was the Intent-To-Treat (ITT) population, which comprised all subjects who were randomized. All efficacy analyses were conducted on the ITT population. In addition, efficacy analyses were also conducted on the evaluable population which comprised subjects who were randomized, had pain or relief assessments after dosing, and stayed on the study for at least one hour.

One-way analysis of variance (ANOVA) was performed on TOTPAR, SPID and VAS-SPID. Each combination treatment was compared with the tapentadol alone treatment with Fisher's least significant difference test (LSD), using Hochberg's (Biometrik 75: 800 (1988)) procedure to control the family-wise type 1 error. For all pair wise comparisons, the error mean square from the overall analysis of variance with all treatments were used as the estimate of error variance. Similar techniques were used for pain relief, PID and VAS-PID.

Time to remedication (or rescue medication) was analyzed using the Kaplan-Meier estimate to compute the survival distribution function. The distribution was compared among groups using the Log Rank Test. A subject was considered censored at eight hours if remedication had not occurred. Pairwise comparisons were made using the LIFETEST methodology. Hochberg's procedure was used to control the family-wise type 1 error. Time to Onset of Meaningful Relief (determined by the stopwatch) was similarly analyzed. Subjects who did not achieve meaningful relief or take rescue medications were considered treatment failures and were assigned a value of 8 hours or the time when the rescue medication was taken. In all the above analyses baseline pain intensity could be used as a stratification factor. The distribution of Starting Pain Intensity, Global Evaluations and Adverse Side Effects were displayed. The sample size was estimated from historical data and from practical considerations rather than from calculation of expected measured differences.

Efficacy analyses were conducted on 2 populations: the ITT population and the evaluable population (Table 1). The ITT population comprised all subjects who were randomized, took study drug, and had post-randomization data. The evaluable population comprised of only the ITT subjects who had pain or relief assessments after dosing and did not take rescue medication within the first hour following dosing.

Study 4; Treatment of Humans with Tapentadol+Pregabalin in Combination with Naltrexone.

The study was of double-blind, randomized, placebo-controlled, and two-period cross-over design. After a 12 hours, 170 diabetic patients (90 men, 80 women with type 2 diabetes, age [mean±SE] 61.7±1.6 years, duration of diabetes 8,8±1.5 years, duration of painful neuropathy 2.2±0.4 years) were randomized to receive either Group 1 (Placebo+Placebo), Group 2 (Tap 100 mg+P 250 mg)+Placebo), Group 3 (Tap 100 mg+P 250 mg)+Naltrexone (N2) (0.01 mg), Group 4 (Tap 100 mg+P 250 mg)+Naltrexone (N2) (0.1 mg), Group 5 (Tap 100 mg+P 250 mg)+Naltrexone (N2) (1 mg). Among those entered, 154 patients successfully completed the study. Bihourly pain and other sensory symptoms were assessed using a visual analog scale (VAS). The patient characteristics are shown in Table 4.

| Patient Characteristics | |
|---|---|
| Number of patients | 150 |
| Age (years) | 63.7 ± 1.8 (41-76)* |
| Sex | 70 males, 80 females |
| BMI (kg/m2) | 32.8 ± 1.4 |
| Type of diabetes | 2 type 1, 20 type 2 |
| Duration of diabetes (years) | 9.1 ± 1.5 |
| Duration of neuropathy (years) | 3.0 ± 0.5 |
| Duration of neuropathic pain (years) | 2.5 ± 0.4 |
| Treatment order | 10 ISDN, 12 placebo |
| HbA1c (%)† | |
| At study entry | 7.8 ± 0.3 |
| At study completion | 8.1 ± 0.4 |

*Data are n or means, SE. Age Range;
†HbA1c Reference Range 4.2-5.9%.

Every one of the patients had long history of difficult-to treat painful neuropathy and had tried various drugs such as acetaminophen, duloxetine, amitriptyline or gabapentin and had discontinued because the symptoms were unresponsive or due to unacceptable side effects. Eligible subjects included type 1 and type 2 diabetic patients not on any other medications for their neuropathic pain and with stable diabetic control. Exclusion criteria included erratic glycemic control, peripheral vascular disease (PVD) with absent foot pulses, presence of active foot ulceration, treatment with sublingual glyceryl trinitrate, patients on erectile dysfunction drugs, factors affecting the patient's evaluation of pain, and the presence of other causes of peripheral neuropathies. No major changes made for diabetes treatment during the duration of the study.

Patients were assessed neurologically at the beginning of the run in period after which, the patients were randomly allocated to receive the treatments either Group 1 (Placebo+Placebo), Group 2 (Tap 100 mg+P 250 mg, Example 3)+Placebo), Group 3 (Tap 100 mg+P 250 mg, Example 3)+Naltrexone (N2) (0.01 mg), Group 4 (Tap 100 mg+P 250 mg, Example 3)+Naltrexone (N2) (0.1 mg), Group 5 (Tap 100 mg+P 250 mg, Example 3)+Naltrexone (N2) (1 mg). A 10-cm visual analog scale (VAS) was recorded biweekly by the patients for pain, where 0 means no pain at all and 10 means the most severe pain ever experienced. The treatment effect was defined to be the difference between the final score and the baseline score on the Lickert scale for each treatment phase.

The objectives of the inventions are met for the fixed dose combination comprising a Tapentadol and Pregabalin and Naltrexone produced statistically significant and clinically meaningful reductions, compared to the tapentadol+pregabalin, for the primary efficacy variable in pain intensity associated with diabetic neuropathy. We considered that a clinically significant benefit would be a reduction in the pain score (VAS) of at least 15% compared to the other treatments.

Study 5; Treatment of Humans with Tapentadol with Methylnaltrexone

In order to establish the invention, Nectid conducted a human clinical study involving 304 pain patients and among them 253 patients completed the trial. The patients were administered with tapentadol alone or in combination with three different doses of naltrexone; 0.01, 0.1 and 1.0 mg. The analgesic efficacy of the co-administered combination of tapentadol and different doses of methylnaltrexone hydrochloride, in comparison with positive and negative controls, was measured. The effect of such combination on constipation was also measured.

In this randomized, double-blind, active-controlled and placebo-controlled, parallel-group study, study, one objective was to determine whether methylnaltrexone hydrochloride (hereafter referred to as MNTX), enhance the analgesic properties of tapentadol hydrochloride (hereafter referred to as Tap) in human subjects/patients with pain following dental surgery. Another objective was to evaluate whether methylnaltrexone reduced tapentadol induced constipation in humans.

Three hundred four (304) subjects were actually entered in the study and among them 254 completed the study. A positive control Tapentadol and a negative control (placebo) were used and the human subjects were randomized into one of the following five treatment groups: The numbers of subjects were actually assigned to the five treatment groups are as follows:

Group 1: Placebo with Placebo: 51
Group 2: T (50 mg) with Placebo: 50
Group 3: T (50 mg) with Methylnaltrexone (0.01 mg): 51
Group 4: T (50 mg) with Methylnaltrexone (0.1 mg): 52
Group 5: T (50 mg) with Methylnaltrexone (1 mg): 50

A positive control (Tapentadol 50 mg, Group 2) was used to determine the sensitivity of the clinical end points. A negative control (placebo, Group 1) was used to establish the frequency and magnitude of changes in clinical end points that may occur in the absence of an active treatment. A single oral dose of study medication was administered when the subject experienced moderate to severe pain following the surgical extraction of three or four third-molars.

Results

The invention is illustrated by the following representative results from clinical studies. The diagrams shown are for illustration purposes only and in no way limit the scope of the invention. A person skilled in the art may easily modify the studies using opioid agonists and antagonists.

Figure 1:
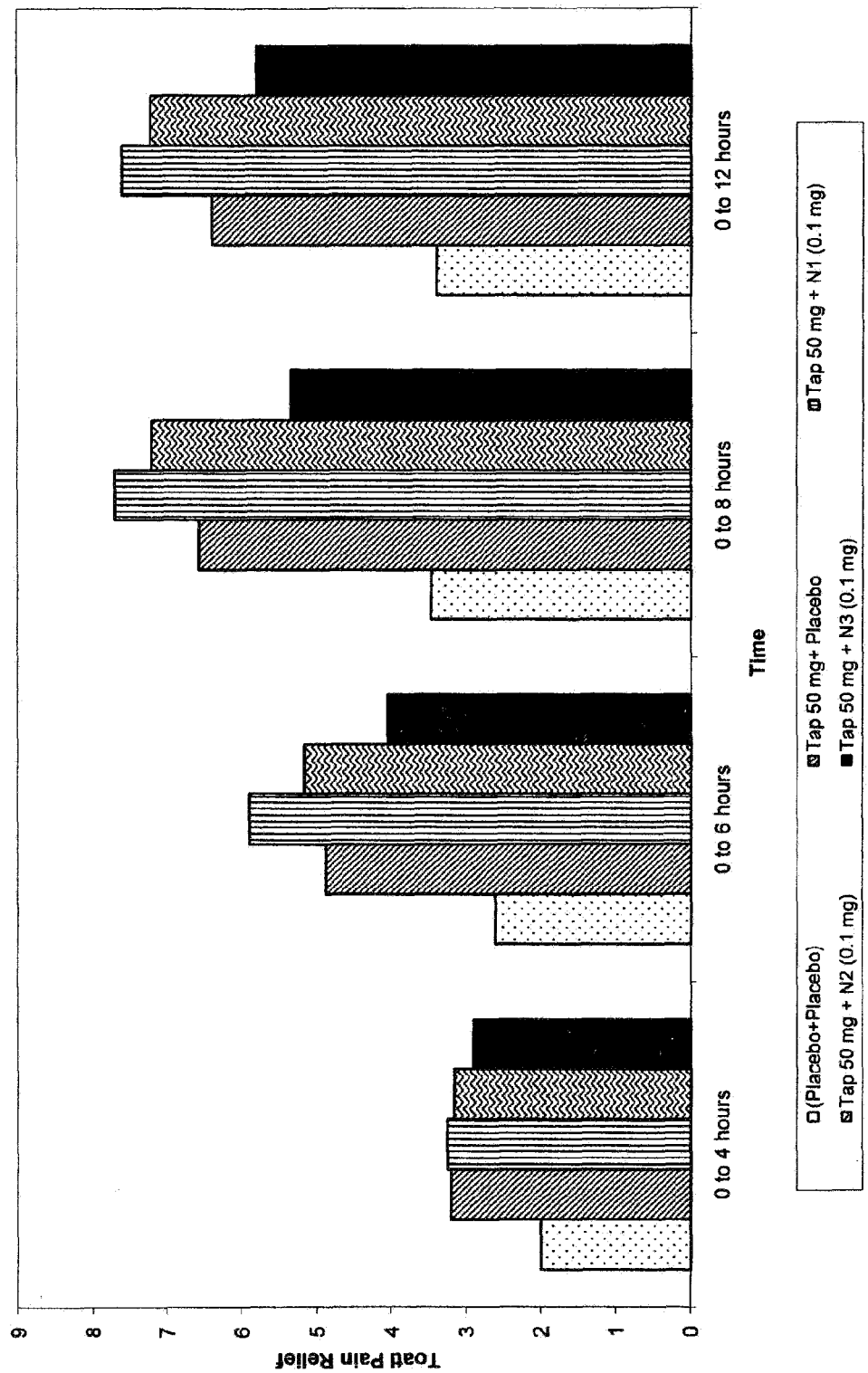
FIG. 1 represents the 4-hour Total Pain Relief Scores (TOTPAR) for Tapentadol 50 mg with Naloxone (0.1 mg), with Naltrexone (0.1 mg), and with Nalmefene (0.1 mg).

FIG. 1 represents the 4-hour Total Pain Relief Scores (TOTPAR) for Group 1: Placebo with Placebo, Group 2: Tapentadol (50 mg) with Placebo, Group 3: Tapentadol (50 mg) with Naloxone (0.1 mg), Group 4: Tapentadol (50 mg) with Naltrexone (0.1 mg), Group 5: Tapentadol (50 mg) with Nalmefene (0.1 mg).

Figure 2:
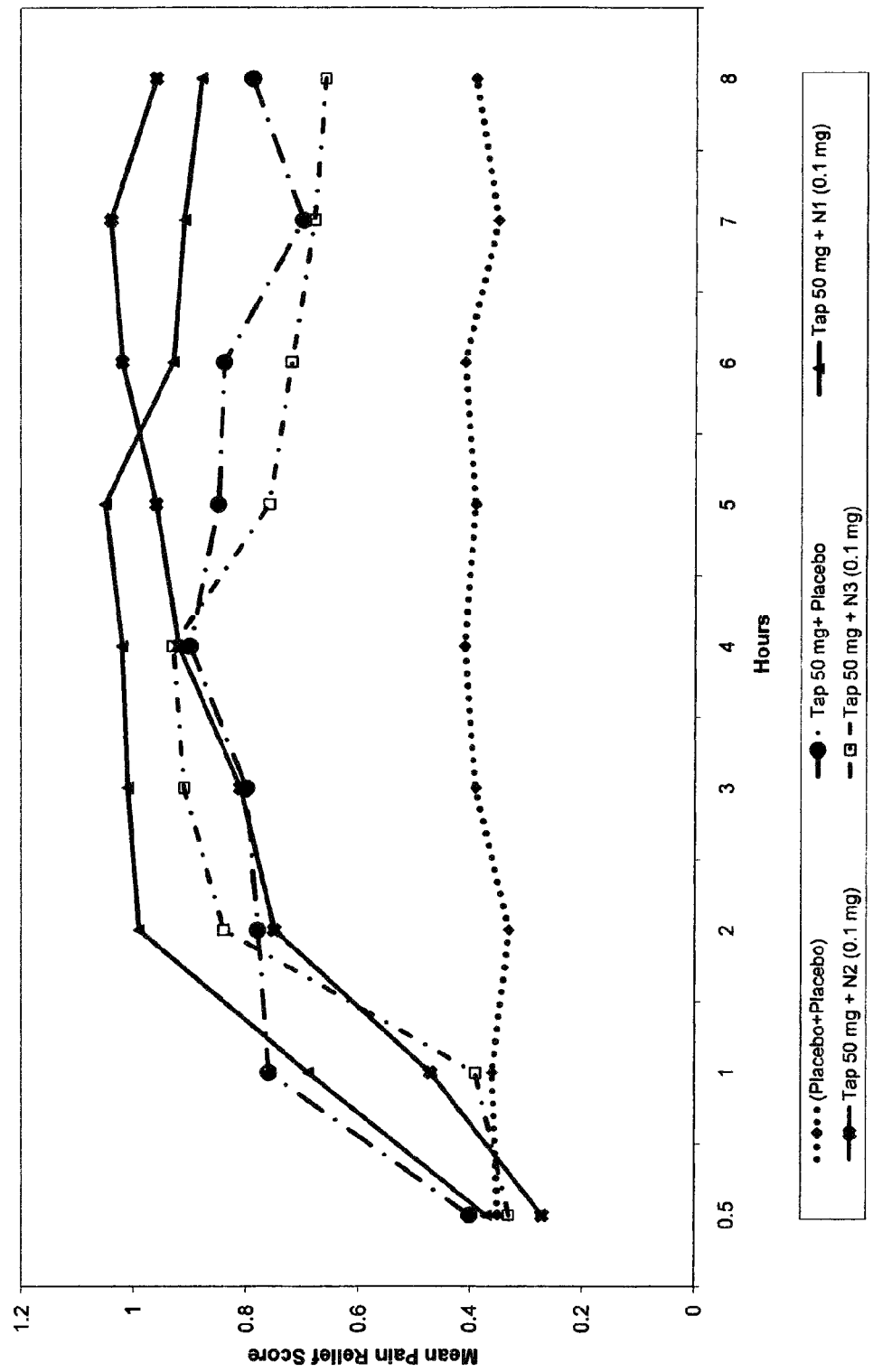
FIG. 2 represents the hourly pain relief scores from 0-12, 0-8 and 0-4 hours for Tapentadol 50 mg with Naloxone (0.1 mg), with Naltrexone (0.1 mg), and with Nalmefene (0.1 mg).

FIG. 2 represents the hourly pain relief scores from 0-12, 0-8 and 0-4 hours for Group 1: Placebo with Placebo, Group 2: Tapentadol (50 mg) with Placebo, Group 3: Tapentadol (50 mg) with Naloxone (0.1 mg), Group 4: Tapentadol (50 mg) with Naltrexone (0.1 mg), Group 5: Tapentadol (50 mg) with Nalmefene (0.1 mg).

Figure 3:
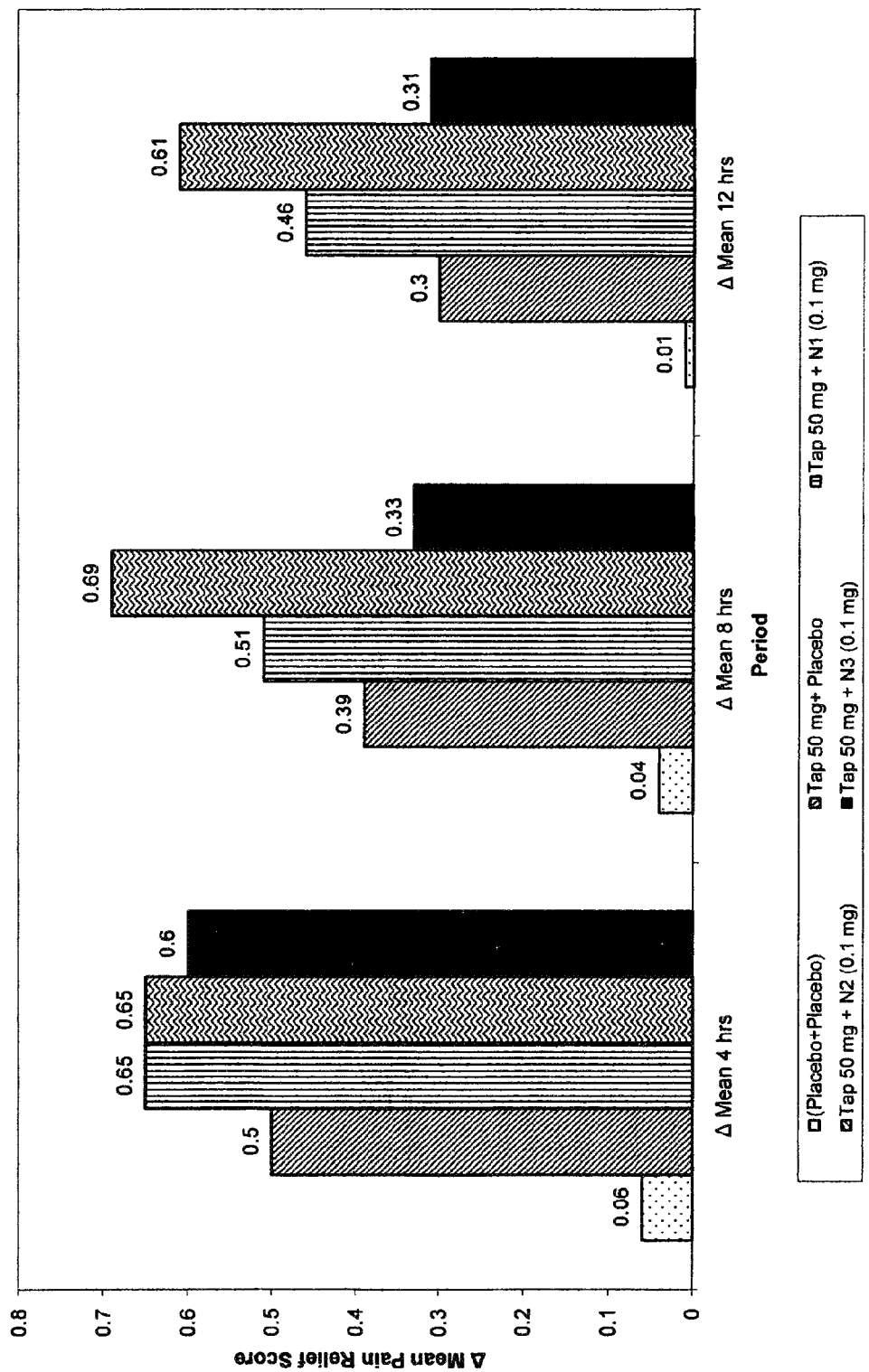
FIG. 3 represents Changes in the Δ mean pain relief scores at four hours, at eight hours and twelve hours Tapentadol 50 mg with Naloxone (0.1 mg), with Naltrexone (0.1 mg), and with Nalmefene (0.1 mg).

FIG. 3 represents Changes in the Δ mean pain relief scores at four hours, at eight hours and twelve hours for Group 1: Placebo with Placebo, Group 2: Tapentadol (50 mg) with Placebo, Group 3: Tapentadol (50 mg) with Naloxone (0.1 mg), Group 4: Tapentadol (50 mg) with Naltrexone (0.1 mg), Group 5: Tapentadol (50 mg) with Nalmefene (0.1 mg).

FIG. 4 shows comparison of key side effects associated with tapentadol with different opioid antagonists.

FIG. 5 represents the 4-hour Total Pain Relief Scores (TOTPAR) for Group 1: Placebo with Placebo, Group 2: (SRT 100 mg, Example 2) with Placebo, Group 3: (SRT 100 mg, Example 2) with Naltrexone N1 (0.1 mg), Group 4: (SRT 100 mg, Example 2) with Naloxone N2 (0.1 mg), Group 5: (SRT 100 mg, Example 2) with Nalmefene N3 (0.1 mg) and Group 6: FDC (SRT 100 mg+Naltrexone N1 (1 mg, Example 7).

FIG. 6 represents the hourly pain relief scores from 0-12, 0-8 and 0-4 hours for Group 1: Placebo with Placebo, Group 2: (SRT 100 mg, Example 2) with Placebo, Group 3: (SRT 100 mg, Example 2) with Naltrexone N1 (0.1 mg), Group 4: (SRT 100 mg, Example 2) with Naloxone N2 (0.1 mg), Group 5: (SRT 100 mg, Example 2) with Nalmefene N3 (0.1 mg) and Group 6: FDC (SRT 100 mg+Naltrexone N1 (1 mg, Example 7).

FIG. 7 represents Changes in the Δ mean pain relief scores at four hours and at eight hours and twelve hours for Group 1: Placebo with Placebo, Group 2: (SRT 100 mg, Example 2) with Placebo, Group 3: (SRT 100 mg, Example 2) with Naltrexone N1 (0.1 mg), Group 4: (SRT 100 mg, Example 2) with Naloxone N2 (0.1 mg), Group 5: (SRT 100 mg, Example 2) with Nalmefene N3 (0.1 mg) and Group 6: FDC (SRT 100 mg+Naltrexone N1 (1 mg, Example 7).

FIG. 8 shows comparison of key side effects associated with slow release tapentadol with different antagonists.

FIG. 9 represents the 4-hour Total Pain Relief Scores (TOTPAR) for Group 1: Placebo with Placebo, Group 2: FDC-Example 4 (Tapentadol (100 mg)+Naproxen 250 mg) with Placebo, Group 3: FDC-Example 4 (Tapentadol (100 mg)+Naproxen 250 mg) with N2 (0.01 mg), Group 4: FDC-Example 4 (Tapentadol (100 mg)+Naproxen 250 mg) with N2 (0.1 mg), Group 5: FDC-Example 4 (Tapentadol (100 mg)+Naproxen 250 mg) with N2 (1 mg).

FIG. 10 represents the hourly pain relief scores from 0-12, 0-8 and 0-4 hours for Group 1: Placebo with Placebo, Group 2: FDC-Example 4 (Tapentadol (100 mg)+Naproxen 250 mg) with Placebo, Group 3: FDC-Example 4 (Tapentadol (100 mg)+Naproxen 250 mg) with N2 (0.01 mg), Group 4: FDC-Example 4 (Tapentadol (100 mg)+Naproxen 250 mg) with N2 (0.1 mg), Group 5: FDC-Example 4 (Tapentadol (100 mg)+Naproxen 250 mg) with N2 (1 mg).

FIG. 11 represents the changes in the Δ mean pain relief scores at four hours and at eight hours and twelve for Group 1: Placebo with Placebo, Group 2: FDC-Example 4 (Tapentadol (100 mg)+Naproxen 250 mg) with Placebo, Group 3: FDC-Example 4 (Tapentadol (100 mg)+Naproxen 250 mg) with N2 (0.01 mg), Group 4: FDC-Example 4 (Tapentadol (100 mg)+Naproxen 250 mg) with N2 (0.1 mg), Group 5: FDC-Example 4 (Tapentadol (100 mg)+Naproxen 250 mg) with N2 (1 mg).

FIG. 12 shows the mean VAS pain score changes in VAS pain score for Group 1 (Placebo+Placebo), Group 2 (FDC-Example 3, Tapentadol 100 mg+Pregabalin 250 mg)+Placebo), Group 3 (FDC-Example 3, Tapentadol 100 mg+Pregabalin 250 mg)+N2 (0.01 mg), Group 4 (FDC-Example 3, Tapentadol 100 mg+Pregabalin 250 mg)+N2 (0.1 mg), Group 5 (FDC-Example 3, Tapentadol 100 mg+Pregabalin 250 mg)+N2 (1 mg).

FIG. 13 shows the Δ mean VAS pain score changes in VAS pain for Group 1 (Placebo+Placebo), Group 2 (FDC-Example 3, Tapentadol 100 mg+Pregabalin 250 mg)+Placebo), Group 3 (FDC-Example 3, Tapentadol 100 mg+Pregabalin 250 mg)+N2 (0.01 mg), Group 4 (FDC-Example 3, Tapentadol 100 mg+Pregabalin 250 mg)+N2 (0.1 mg), Group 5 (FDC-Example 3, Tapentadol 100 mg+Pregabalin 250 mg)+N2 (1 mg).

FIG. 14 represents the 4-hour Total Pain Relief Scores (TOTPAR) for Group 1: Placebo with Placebo, Group 2: Tapentadol (50 mg) with Placebo, Group 3: Tapentadol (50 mg) with Methylnaltrexone (0.01 mg), Group 4: Tapentadol (50 mg) with Methylnaltrexone (0.1 mg), Group 5: Tapentadol (50 mg) with Methylnaltrexone (1 mg).

FIG. 15 represents the hourly pain relief scores from 0-12, 0-8 and 0-4 hours for Group 1: Placebo with Placebo, Group 2: Tapentadol (50 mg) with Placebo, Group 3: Tapentadol (50 mg) with Methylnaltrexone (0.01 mg), Group 4: Tapentadol (50 mg) with Methylnaltrexone (0.1 mg), Group 5: Tapentadol (50 mg) with Methylnaltrexone (1 mg).

FIG. 16 represents Changes in the Δ mean pain relief scores at four hours, at eight hours and twelve hours for Group 1: Placebo with Placebo, Group 2: Tapentadol (50 mg) with Placebo, Group 3: Tapentadol (50 mg) with Methylnaltrexone (0.01 mg), Group 4: Tapentadol (50 mg) with Methylnaltrexone (0.1 mg), Group 5: Tapentadol (50 mg) with Methylnaltrexone (1 mg).

FIG. 17 shows comparison of the extent of tapentadol induced side effect; constipation with different doses of methylnaltrexone.

I claim:

1. A dosage form comprising at least one form of tapentadol and at least one opioid antagonist, wherein the at least one form of tapentadol is present in the dosage form in an amount that is, along with the at least one opioid antagonist, effective to treat pain, and the at least one opioid antagonist is present in the dosage form in an amount that is effective to improve the efficacy and/or reduce the side effects of the at least one form of tapentadol, wherein the side effects are at least one member selected from the group consisting of nausea, vomiting, dizziness, headache, somnolence and pruritus.

2. A method for treating pain in a human subject comprising administering to the human subject a dosage form of claim 1.

3. A method of claim 2, wherein tapentadol is present in an optimal or suboptimal amount.

4. A dosage form of claim 1, wherein the said dosage form provides effective pain relief for at least 12 hours, when administered to a human patient.

5. A dosage form of claim 1, wherein the said dosage form provides effective pain relief for up to 24 hours, when administered to a human patient.

6. A dosage form comprising at least one form of tapentadol and at least one opioid antagonist, wherein the dosage exhibits a dissolution profile, when measured in a USP Type II paddle apparatus at 100 rpm at 37° C. in 900 ml simulated gastric fluid/simulated intestinal fluid (SGF/SIF) combination, such that about 8% of tapentadol is released after two hours, about 22% of tapentadol is released after 4 hours, about 48% of tapentadol is released after 8 hours, about 70% of tapentadol is released after 12 hours, about 78% of tapentadol is released after 16 hours, and not less than 80% of tapentadol is released after 20 hours.

7. A method for treating pain in a human subject comprising administering to the human subject a dosage form of claim 6.

8. A dosage form of claim 1, wherein the antagonist is selected from the group consisting of naloxone, naltrexone, nalmefene, methylnaltrexone, nalide, nalmexone, nalorphine, and nalbuphine.

9. A dosage form of claim 1, wherein the dosage form, upon administration, results in an adverse event profile which is better than the adverse event profile resulting from the administration of a dosage form that is devoid of an antagonist.

10. A dosage form of claim 1, wherein the dosage form, upon administration, results in fewer occurrences of dizziness or vertigo than would result from the administration of a dosage form that is devoid of an antagonist.

11. A dosage form of claim 1, wherein the dosage form, upon administration, results in fewer occurrences of nausea than would result from the administration of a dosage form that is devoid of an antagonist.

12. A dosage form of claim 1, wherein the dosage form, upon administration, results in fewer occurrences of vomiting than would result from the administration of a dosage form that is devoid of an antagonist.

13. A dosage form of claim 1, comprising an optimal or suboptimal amount of at least one form of tapentadol, wherein the dosage form, upon administration, results in fewer occurrences of headache than would result from the administration of a dosage form that is devoid of an antagonist.

14. A dosage form of claim 1, comprising an optimal or suboptimal amount of at least one form of tapentadol, wherein the dosage form comprises from about 25 to about 800 mg of one form of tapentadol.

15. A method of claim 2, wherein the route of administration is oral, sublingual, intramuscular, subcutaneous, buccal, intravenous or transdermal.

16. A pharmaceutical kit comprising at least one form of tapentadol and at least one opioid antagonist.

17. A dosage form of claim 1, further comprising at least one additional drug.

18. A method for treating pain in a human subject comprising administering to the human subject a dosage form of claim 17.

19. A method of claim 18, wherein the said at least one additional drug is a second analgesic selected from the group consisting of an NSAID, Acetaminophen, a GABA analogue, a Serotonin Norepinephrine reuptake inhibitor (SNRI), a Cyclo-oxygenase-(COX)-inhibiting nitric oxide donator, a HT Agonist and a Proton Pump Inhibitor, tramadol, hydromorphone, faxeladol, axomadol, oxycodone, hydrocodone, hydromorphone, fentanyl, morphine, pharmaceutically acceptable salts thereof and mixtures thereof.

20. A method of claim 19, wherein the said second analgesic is selected from the group consisting of an NSAID, Acetaminophen, a GABA analogue, a Serotonin Norepinephrine reuptake inhibitor (SNRI), a Cyclo-oxygenase-(COX)-inhibiting nitric oxide donator, a HT Agonist and a Proton Pump Inhibitor, tramadol, hydromorphone, hydromorphone, faxeladol, axomadol, oxycodone, hydrocodone, fentanyl, morphine, pharmaceutically acceptable salts thereof and mixtures thereof.

21. A method of claim 18, wherein the said antagonist is selected from the group consisting of naloxone, naltrexone, nalmefene, methylnaltrexone, nalide, nalmexone, nalorphine, and nalbuphine.

22. A method of increasing the efficacy of tapentadol against pain and/or reducing the side effects of taking tapentadol, said side effects being selected from the group consisting of nausea, vomiting, dizziness, headache, somnolence and pruritus, said method comprising incorporating at least one opioid antagonist in an effective amount therefor into a dosage form comprising at least one form of tapentadol present in the dosage form in an amount of said at least one form of tapentadol effective to treat pain, and administering said dosage form to a patient in need thereof.

* * * * *